(12) United States Patent
Stinchcomb et al.

(10) Patent No.: US 8,653,271 B2
(45) Date of Patent: Feb. 18, 2014

(54) ENHANCING TRANSDERMAL DELIVERY OF OPIOID ANTAGONISTS AND AGONISTS USING CODRUGS LINKED TO BUPROPION OR HYDROXYBUPROPION

(75) Inventors: Audra L. Stinchcomb, Lexington, KY (US); Peter A. Crooks, Nicholasville, KY (US); Mohamed O. Hamad, Lexington, KY (US); Paul K. Kiptoo, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1255 days.

(21) Appl. No.: 11/907,954

(22) Filed: Oct. 18, 2007

(65) Prior Publication Data
US 2009/0017102 A1 Jan. 15, 2009

Related U.S. Application Data

(60) Provisional application No. 60/853,761, filed on Oct. 24, 2006, provisional application No. 60/852,394, filed on Oct. 18, 2006.

(51) Int. Cl.
*C07D 489/00* (2006.01)
*C07D 489/02* (2006.01)
*C07D 489/12* (2006.01)
*A61K 31/485* (2006.01)

(52) U.S. Cl.
USPC .................. 546/44; 546/45; 546/46; 514/282

(58) Field of Classification Search
USPC ................................ 546/45, 44, 46; 514/282
See application file for complete search history.

(56) References Cited

U.S. PATENT DOCUMENTS 4,638,043 A * 1/1987 Szycher et al. ................. 528/75

OTHER PUBLICATIONS

Lau et. al. "Scope and Limitations of the Co-Drug Approach to Topical Drug Delivery" Current Pharmaceutical Design, 2008, 14, 794-802.*
Hamad, P. Kiptoo, A. Stinchcomb, P. Crooks "Synthetic Strategies for the Preparation of "Gemini" Codrugs of Naltrexone, and Heterocodrugs of β-Naltrexol With Hydroxybupropion for Transdermal Delivery" "http://www.aapsj.org/abstracts/AM_2005/AAPS2005-001891.pdf" online, accessed Feb. 9, 2011.*
"http://web.archive.org/web/20051013071834/aaps.org" online, Oct. 13, 2005, accessed Feb. 9, 2011.*
"http://www.aapsj.org/abstracts/AM_2005/" online, Thursday, May 5, 2005 9:04 PM, accessed Feb. 9, 2011.*

* cited by examiner

*Primary Examiner* — David K O Dell
(74) *Attorney, Agent, or Firm* — Crowell & Moring LLP

(57) ABSTRACT

The present invention is directed to novel codrugs comprising bupropion or hydroxybupropion and an opioid antagonist or an opioid agonist joined together by chemical bonding. The codrugs provide a significant increase in the transdermal flux across human skin, as compared to the basic opioid antagonist or opioid agonist.

13 Claims, 14 Drawing Sheets

1; Naltrexone (NTX)

2; 6-β-Naltrexol (NTXOL)

3; Bupropion (BUP)

4; Hydroxybupropion (BUPOH)

14

15

16

17

[a]Reagents and conditions: (a) CH$_2$Cl$_2$ or THF, Base = TEA or Pyridine, t = 0 °C, Argon.
(b) CH$_2$Cl$_2$, TEA, t = 0 °C, Argon, Naltrexone. (c) CH$_2$Cl$_2$, TEA, t = 0 °C, Argon, Naltrexol.
(d) -HCl

11; Naltrexone Duplex
13; Naltrexol Duplex

<sup>a</sup>Reagents and conditions: (a) NaOH, formamidinesulfinic acid, 80-85°C, 1.5 h. (b) COCl₂, CH₂Cl₂, TEA, t = 0 °C, Argon.

(a) COCl₂, CH₂Cl₂, TEA, t = 0 °C, Argon. (b) NTX, CH₂Cl₂, TEA, t = 0 °C, Argon. (c) NTXOL, CH₂Cl₂, TEA, t = 0 °C, Argon.

[a] A schematic diagram showing stepwise hydrolytic cleavage of the carbonate codrug 25, into NTX and BUOH in isotonic phosphate buffer, pH 7.4 at 32°C.

ENHANCING TRANSDERMAL DELIVERY OF OPIOID ANTAGONISTS AND AGONISTS USING CODRUGS LINKED TO BUPROPION OR HYDROXYBUPROPION

CROSS REFERENCE TO RELATED APPLICATIONS

This application claims priority under 35 U.S.C. §119 to U.S. Provisional Application No. 60/853,761 filed Oct. 24, 2006 and U.S. Provisional Application No. 60/852,394 filed Oct. 18, 2006, the disclosures of which are incorporated herein by reference.

GOVERNMENT INTERESTS

A portion of this invention was made with U.S. Government support under a grant from the National Institutes of Health under NIH Grant R01AA013853. The Government may have certain rights in this invention.

FIELD OF THE INVENTION

This invention relates to novel codrugs, and more particularly to novel codrugs comprising bupropion or hydroxybupropion and an opioid antagonist or an opioid agonist joined together by chemical bonding. The codrugs possess increased bioavailability as compared to the parent drugs.

BACKGROUND OF THE INVENTION

Transdermal delivery is desirable to reduce the side effects associated with the oral administration of drugs. Such side effects can include abdominal pain, nausea and vomiting. Further, transdermal delivery offers a patient freedom from injections and surgical implantations. Transdermal delivery also bypasses the significant metabolism associated with oral administration of drugs. Transdermal delivery is generally provided through a transdermal patch which provides sustained release of a drug.

Following its application to the skin, the therapeutic efficacy of a drug for transdermal delivery mainly depends on its ability to penetrate the skin fast enough to provide the plasma concentrations required to elicit the desired pharmacological activity. A large majority of drugs are unable to cross the skin at therapeutic rates due to the barrier imposed by the skin's outer stratum corneum layer. Thus, the main challenge in transdermal drug delivery is providing sufficient drug penetration across the skin. Skin permeability can be increased through the use of chemical enhancers, electrical enhancers via electroporation or iontophoresis, ultrasonic enhancers, and a variety of other approaches. Although these enhancement technologies are still under active investigation, delivering macromolecules into the skin remains a significant challenge. See, e.g., Park et al., J. Control. Release 104 (2005) 51-66 and Martanto et al., Pharm. Res. 21 (2004). One of the strategies used to enhance skin permeation of poorly permeable drugs is the codrug approach.

A codrug comprises two different drugs within a single chemical entity. The two drugs may be connected either directly or by means of a cleavable, biolabile covalent linker. Many diseases are treated by a combination of therapeutic agents that are co-administered in separate dosage forms. However, there are potential advantages in delivering the co-administered agents as a single chemical entity. One advantage is that often, when the two drugs are chemically linked together in the codrug structure, the resulting physicochemical and pharmacokinetic properties of the codrug are superior to those of the individual parent drugs. Thus, careful design of the codrug entity can afford a unique product that may have superior physicochemical properties for drug delivery, compared to those of the individual drug entities themselves, leading to improved pharmaceutical properties. In addition, there are also other factors, such as the ability to control drug delivery by appropriate design of the biolabile linker(s) connecting the two drug entities, and the effect that simultaneous delivery of the two drugs, as one chemical entity, will have on the pharmacokinetics of each respective drug. Because the skin and plasma have an abundance of esterase enzymes, codrugs with esterase-susceptible linkages can be cleaved by these enzymes to release the active parent drugs in tissue and plasma.

A codrug or a mutual prodrug consists of two drugs chemically linked together in order to improve the drug delivery properties of one or both drugs. This unique concept of a codrug has been utilized to improve ocular delivery of an antiglaucoma agent, ethacrynic acid (Cynkowska et al., Bioorganic & Medicinal Chemistry Letters 15 (2005) 3524-3527). Other examples of codrugs include facilitated gastrointestinal absorption of low molecular weight heparin (LMWH) via conjugation to deoxycholic acid (DOCA) to form LMWH-DOCA (Lee et al., J. Control. Release 111 (2006) 290-298) and dual-acting thromboxane antagonist-synthase inhibitors (Brown et al., Bioorganic & Medicinal Chemistry Letters 6 (1996) 273-278).

Opioid agonists are useful for treatment of a number of conditions, including chronic pain, acute pain and depression. Opioid antagonists are useful for treatment of alcohol dependence, opioid addiction, and smoking. Naltrexone (NTX), for example, is an opioid antagonist used in the treatment of opiate addiction and alcohol dependence (Volpicelli et al., Arch Gen Psychiatry 49 (1992) 876-80 and Wand et al., Alcohol Clin Exp Res 24 (2000) 1385-91). 6-β-naltrexol (NTXOL) is the active metabolite of NTX (Volpicelli, Lancet 346 (1995) 456 and Verebey et al., Clin Pharmacol Ther 20 (1976) 315-28). Naltrexone is currently available as REVIA®, an FDA approved 50 mg tablet of Naltrexone Hydrochloride, and as VIVITROL™, the recently FDA approved 28-day controlled release 380 mg depot form of Naltrexone. However, REVIA® is poorly bioavailable, with documented side effects (PDR, Medical Economics, 1996, 2229-2233, New Jersey). In addition, although long-lasting Naltrexone depot formulations have shown plasma levels for up to 30 days (Galloway et al., BMC Psychiatry 5 (2005) 18), once VIVITROL™ is injected, it cannot be easily discontinued without painful surgical removal. There is a need for methods for transdermally transporting a therapeutically effective amount of opioid antagonists and agonists, such as Naltrexone, in order to provide benefits such as controlled release, reduced side effects, and the ability to readily discontinue therapy.

Bupropion (BUP) is an aminoketone used as an antidepressant and non-nicotine aid to smoking cessation (Johnston et al., Nicotine Tob Res 3 (2001) 131-40). The pharmacological activity of BUP might be due to, or receive substantial contributions from its major active human metabolite, hydroxybupropion (BUPOH) (Schroeder, J Clin Psychiatry 44 (1983) 79-81 and Belson and Kelley, J Emerg Med 23 (2002) 223-30). Both BUP and BUPOH have excellent physicochemical properties that allow for transdermal delivery, and chemical linkage to BUP or BUPOH should improve the skin permeability characteristics of opioid antagonists and agonists.

The present invention is directed to novel codrugs comprising bupropion or hydroxybupropion and an opioid antagonist or an opioid agonist joined together by chemical bonding. The codrugs provide a significant increase in the transdermal flux across human skin, as compared to the basic opioid antagonist or opioid agonist. Preferably, the opioid antagonist is NTX or NTXOL. The codrug of the present invention may increase the transdermal drug delivery rate either by a solubility improvement or by a permeability improvement, or a combination of both.

SUMMARY OF THE INVENTION

In one aspect, the present invention provides a novel codrug, which improves the oral bioavailability of the component drugs. The term "codrug" as used in the specification and claims means two different drugs joined together by chemical bonding. In the codrug of the present invention, one of the drugs is BUP or BUPOH. The other drug is an opioid antagonist or an opioid agonist. The drugs must have one or more connecting bonds or groups. On introduction of the codrug into the body, the chemical bond is disrupted and the drugs become available for their intended purposes.

The present invention further provides for a method for delivery of the codrug components by biotransforming the codrug into two active drug molecules by hydrolysis or enzymatic digestion. The term "biotransforming" as used herein means using water or enzymes to cleave the connecting bond or group, thereby causing the codrug to be transformed into the active parent drug molecules.

DESCRIPTION OF THE INVENTION

Figure 1:
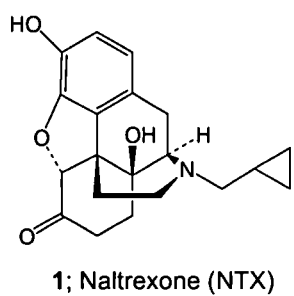
FIG. 1 shows chemical structures of naltrexone (NTX, 1), 6-β-naltrexol (NTXOL, 2), bupropion (BUP, 3), and hydroxybupropion (BUPOH, 4).
Figure 1:
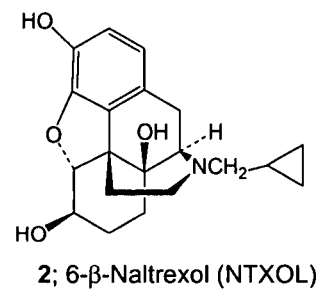
Figure 1:
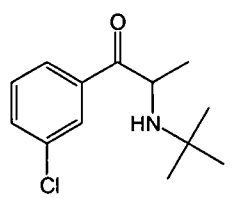
Figure 1:
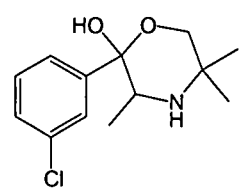

The present invention relates to codrugs comprising BUP or BUPOH and an opioid antagonist or an opioid agonist joined together by chemical bonding. According to the present invention, it has been discovered that the novel codrugs of the invention provide a significant increase in the transdermal flux of the codrugs across human skin, as compared to the basic opioid antagonists and agonists.

Preferably, the codrug comprises one molecule of BUP or BUPOH and one molecule of an opioid antagonist or an opioid agonist joined together by chemical bonding. BUPOH is preferred.

Suitable opioid agonists and antagonists include Naltrexone, Buprenorphine, Butorphanol, Codeine, Dihydrocodeine, Dihydromorphine, Ethymorphine, Hydromorphone, Levallorphan, Levorphanol, Nalbuphine, Nalmefene, Nalorphine, Naloxone, 6-β-Naltrexol, Phenazocine, Pholcodine, or 6-α-Naltrexol. Preferred opioid antagonists are Naltrexone and 6-β-Naltrexol. 6-β-Naltrexol is particularly preferred.

The codrug comprises one or more connecting bonds or groups. The BUP or BUPOH and opioid antagonist or opioid agonist can be linked together via one or more cleavable linker moieties such as ester, thioester, carbonate, carbamate, thiocarbamate, amide, thioamide, ureide, or any other suitable chemical moieties providing that the chemistry is feasible. Preferably, the codrug comprises a carbonate ester linkage.

The linker moiety is preferably bioconvertible or biolabile. More preferably, the linker moiety is cleavable via hydrolysis or enzymatic digestion.

As shown in the present examples, a codrug comprising one molecule of 6-β-naltrexol and one molecule of BUPOH provides an unexpected increase of 6-β-naltrexol maximum flux rate across the skin. Similar results would be expected for other codrugs set forth above.

The present invention also relates to methods for treating conditions including pain, depression, narcotic dependence and drug addiction. Subjects who can benefit from the methods of the present invention include, for example, mammals, such as humans, particularly humans who are suffering from pain, depression, narcotic dependence, alcohol abuse, and/or alcoholism.

"Treatment" or "treating," as used herein, refers to complete elimination as well as to any clinically or quantitatively measurable reduction in condition for which the subject is being treated. The methods of the present invention involve delivering a therapeutically effective amount of the codrug. A "therapeutically effective amount," as used herein, refers to an amount, determined by one skilled in the art, sufficient for treating the condition for which the subject is being treated.

The codrug can be delivered to a subject transdermally, intravenously, orally, buccally, sublingually, by topical creams, subdermally, as a sustained release depot, ophthalmically, intranasally, aurally, by inhalation, rectally or vaginally. After delivery, the codrug is preferably biotransformed by hydrolysis or enzymatic activity into at least two active drug molecules.

Transdermal delivery is preferred. In a method for transdermal delivery of the codrug, the steps comprise contacting a section of human skin with the codrug and biotransforming the codrug into two drugs by skin enzymes or by hydrolysis of the codrug in the skin. A transdermal patch comprising a suitable substrate and a layer of the codrug can be employed to deliver the codrug to the skin.

The codrug is preferably administered as a pharmaceutical composition comprising pharmaceutically acceptable carriers, diluents, and/or excipients, which are vehicles commonly used to formulate pharmaceutical compositions for animal or human administration. The carriers, diluents and/or excipients are not intended to have biological activity themselves, and are selected so as not to affect the biological activity of the codrug and any other active agent(s). A pharmaceutically acceptable carrier, diluent, and/or excipient as used herein includes both one and more than one such carrier, diluent, and/or excipient. Examples include but are not limited to distilled water, saline, physiological phosphate-buffered saline, Ringer's solutions, dextrose solution, and Hank's solution. Depending upon the manner of introduction, the codrug may be formulated as, for example, a sterile injectable formulation comprising aqueous solutions and/or suspensions containing the active materials in admixture with suitable carriers, diluents, and/or excipients.

The concentration of codrug, the formulation (i.e., a formulation that is therapeutically effective to the subject to which it is administered) and the dose administered can be readily determined by a person of ordinary skill in the art. Typically, dosages used in vitro and in animal models, such as in the experiments provided in the present application, may provide useful guidance in the amounts useful for in vivo administration.

The codrug can be applied to the skin as a topical cream, salve, ointment, gel, or other topical formulation; and/or by using delivery devices such as bandages, occlusive bodies, patches, and/or the like. The area of skin to which the codrug is applied can optional be pre-treated with microneedles or other permeability enhancers (see, e.g., Park et al., J. Control. Release 104 (2005) 51-66 and Prausnitz, Adv. Drug Deliv. Rev. 56 (2004) 581-587).

Illustratively, a codrug composition that is applied to the skin can be formulated as a topical cream, salve, gel, or ointment. The topical formulations can include inert diluents and carriers as well as other conventional excipients, such as wetting agents, preservatives, and suspending and dispersing agents. In addition to the above, generally non-active components, topical formulations containing codrug can further include other active materials, particularly, active materials which have been identified as useful in the treatment of the condition for which the subject is being treated, for example drug and/or alcohol addiction, and which can usefully be delivered transdermally to the subject. For instance, such other active materials can include acamprosate, disulfiram, topiramate, sertraline, rivastigmine, citalopram, and doxepin. The topical formulation can be applied directly to the skin and then optionally covered (e.g., with a bandage of gauze) to minimize the likelihood of its being disturbed. Alternatively, the topical formulation can be coated on the surface of a bandage, gauze, etc., and the bandage, gauze, etc. can then be applied to the skin of the subject such that the topical formulation is in direct contact with the subject's skin.

Alternatively, the codrug can be delivered transdermally to the subject by formulating codrug into a bandage, pad, or other type of patch which can be applied to the subject's skin.

Illustratively, matrix-type transdermal patches, in which the codrug is disposed in an adhesive matrix, can be employed. The matrix-type transdermal patch can further include other active materials for transdermal delivery to the subject with the codrug. Suitable adhesives for use in such matrix-type transdermal patches include polyisobutylenes, acrylates, silicone, and combinations thereof. Still other patches suitable for use in the practice of the present invention include those described in U.S. Pat. No. 5,223,262.

In another illustrative embodiment, the bandage, pad, or other type of patch can be one which is capable of controlling the release of the codrug such that transdermal delivery of the Codrug to the subject is substantially uniform and sustained over a period of at least 12 hours, such as at least 24 hours, at least 48 hours, and/or at least 7 days. Such a bandage, pad, or other type of patch which can be used in the practice of the method of the present invention can take the form of an occlusive body. In practice, the occlusive body which includes the codrug is positioned on the subject's skin under conditions effective to transdermally deliver the codrug to the subject's skin.

Other aspects and advantages of the present invention will be understood upon consideration of the following illustrative examples. The examples are not to be construed in any way as limiting the scope of this invention.

EXAMPLES

Example 1

Synthesis and Hydrolytic Profile of Codrugs of Naltrexone and 6-β-naltrexol with Hydroxybupropion 1.1 Introduction Simultaneous treatment of alcohol abuse and tobacco dependence is considered very desirable because of substantial evidence that smoking is increased significantly during drinking (Mello, et al., *Psychopharmacology* 1987, 93 (1), 8-15). It also appears that alcohol drinking is increased in the presence of nicotine; thus each addiction exacerbates the other (Kozlowski, et al., *J. Subst. Abuse Treat.* 1993, 10 (2), 171-179; Mitchell, et al., *Behav. Pharmacol.* 1995, 6, 359-365; Glautier, et al., *Behav. Pharmacol.* 1996, 7, 144-154; Smith, et al., *Psychopharmacology* 1999, 142, 408-412; and Watson, et al., *Neuropharmacology* 1999, 38, 587-595). Opioid addicts also have a high prevalence of tobacco dependency and associated co-abuse problems, and would benefit from a co-therapy approach. (Frosch, et al., *Clin. Psychopharmacology*. 2000, 8 (1), 97-103).

Naltrexone (NTX, 1) (FIG. 1) is an opioid antagonist used in the treatment of opioid addiction and alcohol dependence (Volpicelli, et al., *Arch Gen Psychiatry* 1992, 49, 876-880). However, NTX is a hepatotoxin that has been demonstrated to have low oral bioavailability, and adverse side effects, such as abdominal pain, constipation, nausea, and vomiting. Transdermal delivery is a desirable alternative route of administration for NTX, since it helps reduce side effects associated with oral therapy, and improves compliance (Rohsenow, et al., *Alcoholism: Clinical and Experimental Research.* 2000, 24(10), 1542-1549). Unfortunately, NTX itself does not have the necessary physicochemical properties that would allow a therapeutic dose of the drug to cross the human skin barrier. In recent years, improved transdermal drug delivery has been achieved utilizing more lipophilic prodrugs of NTX, which are more skin permeable than NTX (Stinchcomb, et al., *J. Pharm. Sci.* 2002, 91, 2571-2578; Pillai, et al., *Pharm. Res.* 2004, 21, 1146-1152; Vaddi, et al., *Pharm. Res.* 2005, 22 (5), 758-765; and Valiveti, et al., *J. Contr. Rel.* 2005, 102(2), 509-520). This same approach can be utilized in the design of synergistic codrugs of either NTX or β-naltrexol (NTXOL, 2) (FIG. 1), the active metabolite of NTX (McCaul, et al., *Alcohol: Clin. Exp. Res.* 2000, 24(9), 1385-1391; Rukstalis, et al., *Clin. Exp. Res.* 2000, 24(10), 1593-1596; Porter, et al., *British*

*Journal of Clinical Pharmacology* 2000, 50(5), 465-471; and Wang, et al., *Journal of Neurochemistry* 2001, 77(6), 1590-1600).

Bupropion (BUP, 3) (FIG. 1) is an antidepressant medication and a therapeutic agent currently used in the treatment of nicotine dependence as a smoking cessation agent. Hydroxybupropion (BUPOH, 4) (FIG. 1), is the major metabolite of BUP, and is believed to contribute to its antidepressant activity, as well as the smoking-cessation properties of BUP (Cooper, et al., Neuropsychopharmacology 1994 (1994), 11 (2), 133-141; Ascher, et al., Journal of Clinical Psychiatry 1995, 56 (9), 395-401; Sanchez and Hyttel, J. Cell. Mol. Neurobiol. 1999, 19 (4), 467-489; Slemmer, et al., JPET 2000, 295(1), 321-327). It is likely that BUP may be acting as a nicotinic receptor antagonist, and that this property is responsible for the smoking cessation properties of the drug (Slemmer, et al., 2000). BUP and BUPOH are drug molecules that are considered ideally suitable, from both a chemical and pharmacological perspective, for covalent linkage to NTX and NTXOL to afford clinically useful codrug entities for the treatment of both alcohol abuse and tobacco dependence. Both NTX and BUP are administered in therapeutic doses that are similar, on a molar ratio basis, indicating that a 1:1 ratio of these two drugs in a codrug entity would have therapeutic potential.

The present invention includes a series of novel NTX and NTXOL codrugs covalently linked to either BUP or BUPOH via an enzymatically cleavable linker moiety. These molecules were designed to determine if such codrugs could increase the delivery rate of NTX and NTXOL across human skin when covalently linked to either BUP or BUPOH. If successful, this approach could improve pharmacotherapy for both alcohol abuse and tobacco dependency by providing a single, clinically effective, transdermal codrug dosage form to treat both co-dependent conditions.

Thus, the main therapeutic goal of this approach was to design a codrug that could afford a transdermal flux from 2.8 to≈12-90 nmol/cm$^2$/hr across the skin, followed by rapid metabolism of the codrug to achieve therapeutically effective levels of the two parent drugs in the body. The conversion of the highly crystalline and high melting NTX to a covalently linked codrug with BUP or BUPOH should afford a lower melting and more lipid soluble molecule. Drugs with high melting points often have corresponding low oil solubilities (Stinchcomb, et al., Pharm. Res. 1995, 2, 1526-1529). Transdermal delivery of a drug is in part related to it's lipid solubility, as this establishes the limit of attainable driving force across the skin (Flynn, In *Principles of Route-to-Route Extrapolation for Risk Assessment.* 1990, Gerrity, T. R.; and Henry, C, J. (eds.), Elsevier, N.Y., 93-127). Increased lipophilicity of a drug causes an increase in its skin permeability up to a maximum. Thus, the codrug design was utilized to push the lipophilicity envelope to its optimal value, in order to take advantage of maximal transdermal flux, but also to avoid problems of viable tissue controlled diffusion. (Stinchcomb, et al., Pharm. Res. 1995, 2, 1526-1529).

1.2 Results and Discussion

Chemistry

A codrug is formed by chemical conjugation of two or more drugs via a suitably designed labile linker unit. The drugs are usually linked via linker moieties, such as ester, carbonate, amide, carbamate, etc., which are then cleaved enzymatically to regenerate the active drug molecules at a required site in the body.

Figure 3:
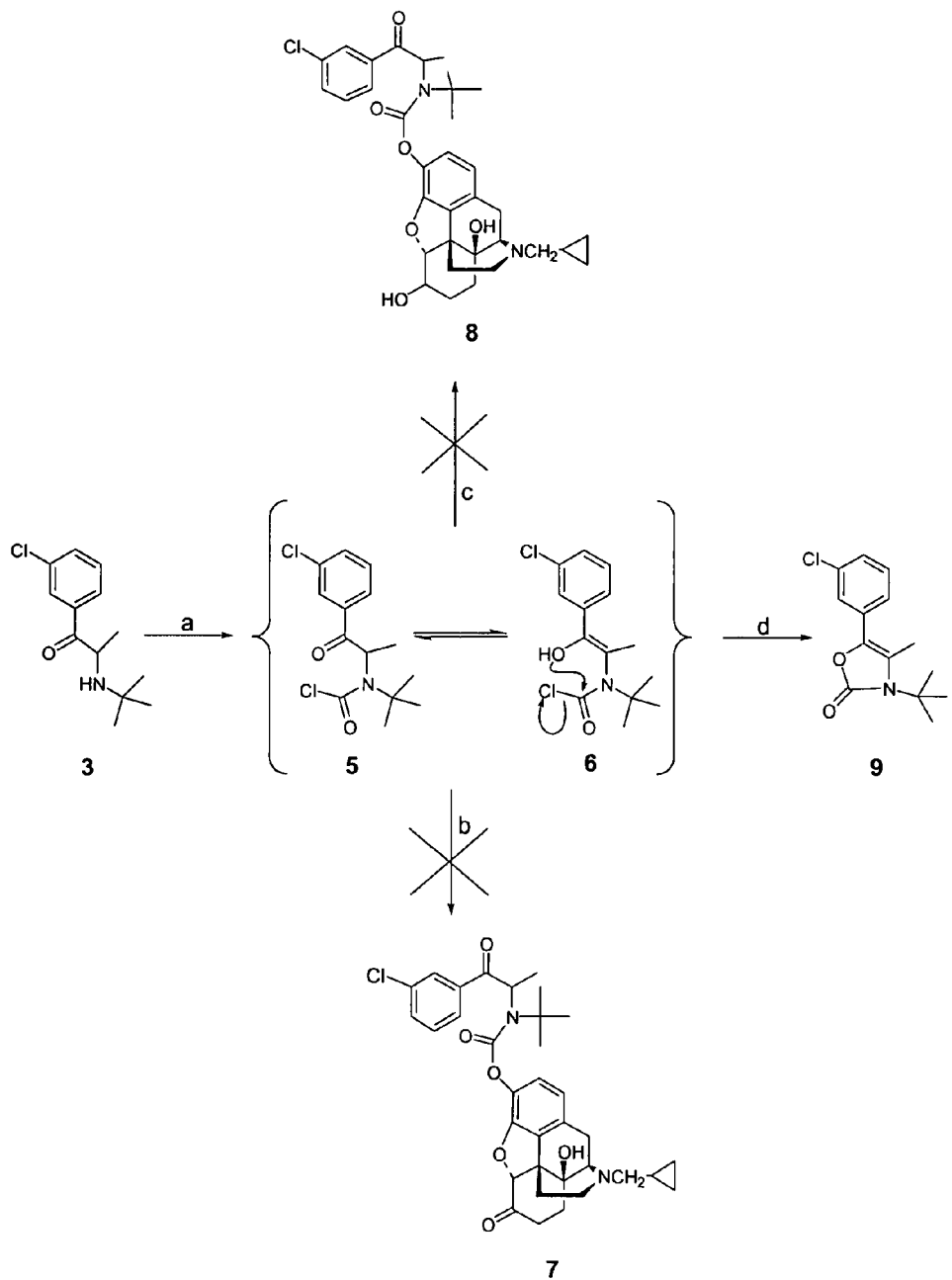
FIGS. 3-6 show codrug synthesis steps.

In efforts to synthesize the carbonate codrugs 7 & 8 (FIG. 3), which are codrugs of BUP covalently linked to either NTX or NTXOL, initial coupling of the two molecules utilizing phosgene as the linker precursor was attempted. Firstly, N-acylation reaction conditions (FIG. 3) utilizing bupropion and phosgene under a variety of conditions and solvents in the presence of triethylamine, followed by addition of NTX, afforded the stable cyclic product 9 and unreacted NTX. When BUP was reacted with phosgene in the absence of NTX, 9 was formed in good yield, rather than the expected chlorocarbonyl intermediate 5 (FIG. 3). This result indicates that the chlorocarbonyl intermediate 7 is not stable enough to be isolated, and its half-life appears to be too short for the reaction with NTX to occur. The formation of 9 can be explained by 5 existing in an equilibrium mixture with its enol tautomer 6, which then undergoes rapid intramolecular O-acylation to form 9.

Figure 4:
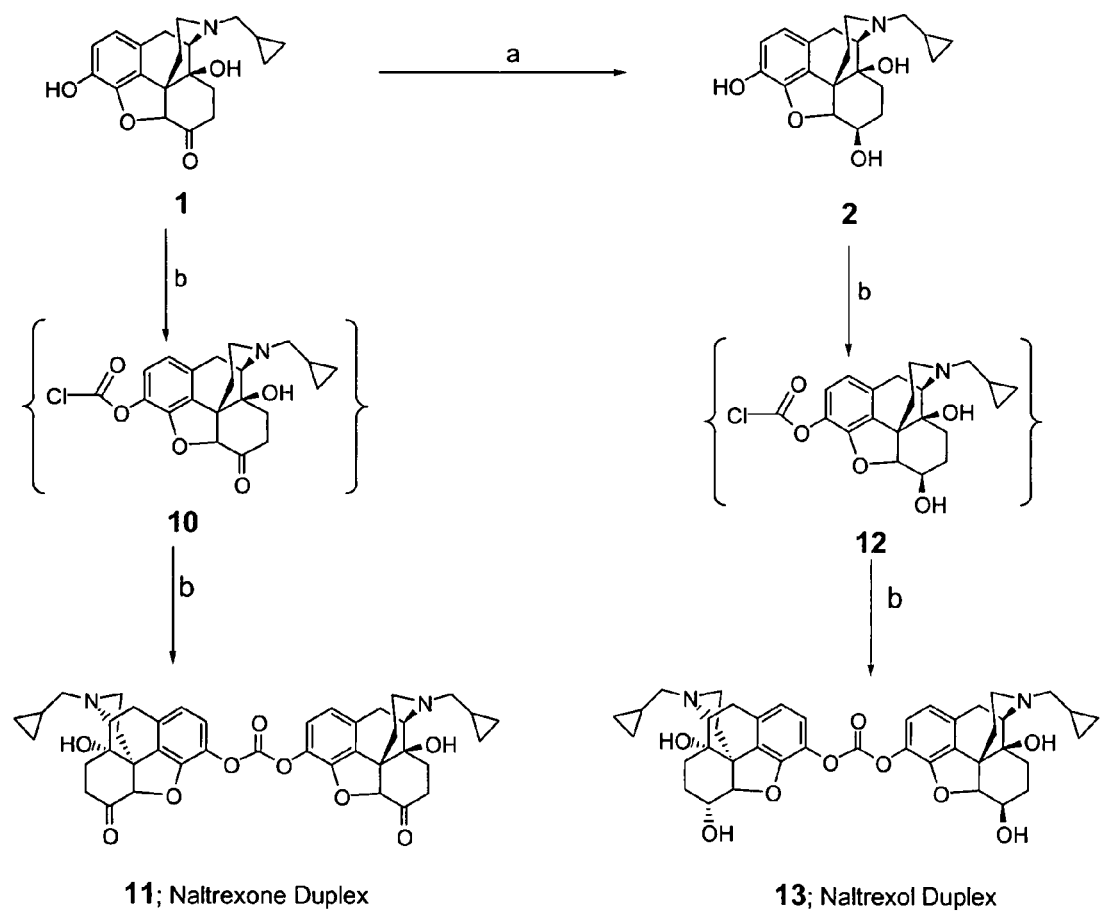

Hussain (Hussain, et al., *J. Pharm. Sci.* 1987, 76, 356-358) and Nelson (Olsen, et al., *J. Med. Chem.* 1990, 33, 737-741) have reported the synthesis of a number of 3-O- and 6-O-ester analogs of NTX and NTXOL. These methodologies do not require protection of the C-14 hydroxyl group, due to its unreactivity, which results from the significant steric hindrance around this functional group. Under the reaction conditions described by Hussain, O-acylation of NTX in the presence of base is regiospecific for the more reactive C-3 phenolic group (as the phenolate anion). Similarly, O-acylation of NTXOL in the presence of base is regiospecific for the 3-OH group (De Costa, et al., *J. Med. Chem.* 1992, 35, 2826-2535). Thus, no prior protection of either the 14- or 6-βOH group in either NTX or NTXOL is required for regiospecific 3-O-acetylation of these molecules. With this in mind, in an alternative strategy, the synthesis of codrugs 7 and 8 via intermediate 10 (FIG. 4), which was formed from the reaction of NTX and phosgene in the presence of triethylamine, was attempted. Under these conditions, the reaction of NTX with phosgene afforded exclusively the dimeric 3-O, 3'-O carbonate ester of NTX (11, FIG. 4) rather than the expected NTX-3-O-chlorocarbonyl intermediate 10. (Hammell, et al., Journal of Controlled Release 2004, 97(2), 283-290). Also, when this reaction was carried out in the presence of BUP, both 11 and 9 were formed, and no codrug could be detected in the reaction mixture. The use of a variety of different reactions conditions in these reactions failed to yield the desired intermediate 10, affording only 11 in good yield. Similarly, when NTXOL was utilized in place of NTX, reaction with phosgene resulted in the formation of the corresponding dimeric 3-O, 3'-O carbonate ester of NTXOL, 13 (FIG. 4).

Figure 2:
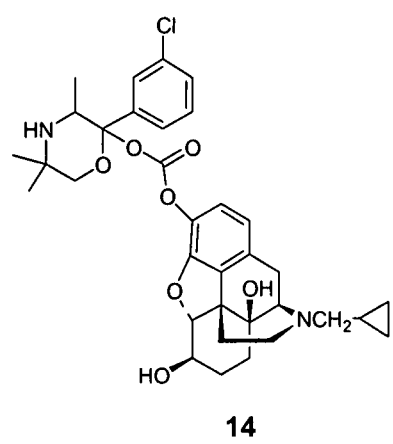
FIG. 2 shows codrugs of hydroxybupropion with naltrexone and naltrexol.
Figure 2:
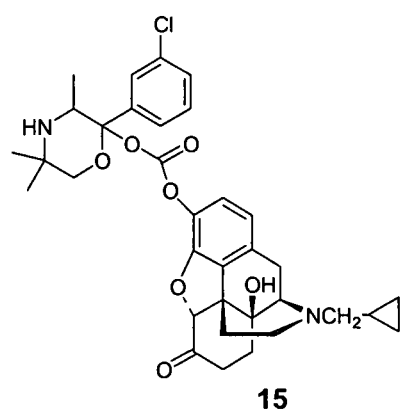
Figure 2:
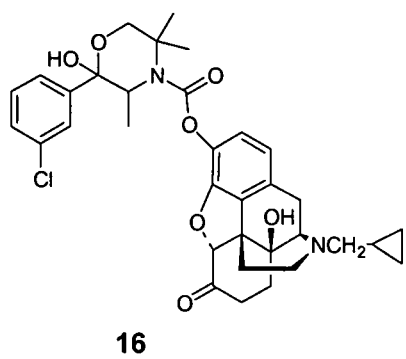
Figure 2:
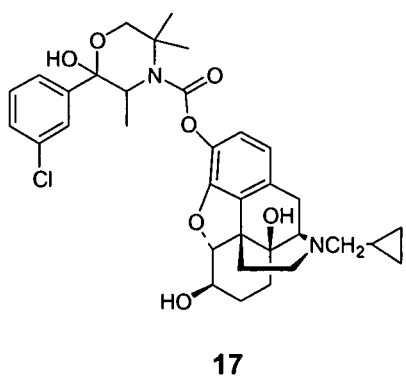
Figure 5:
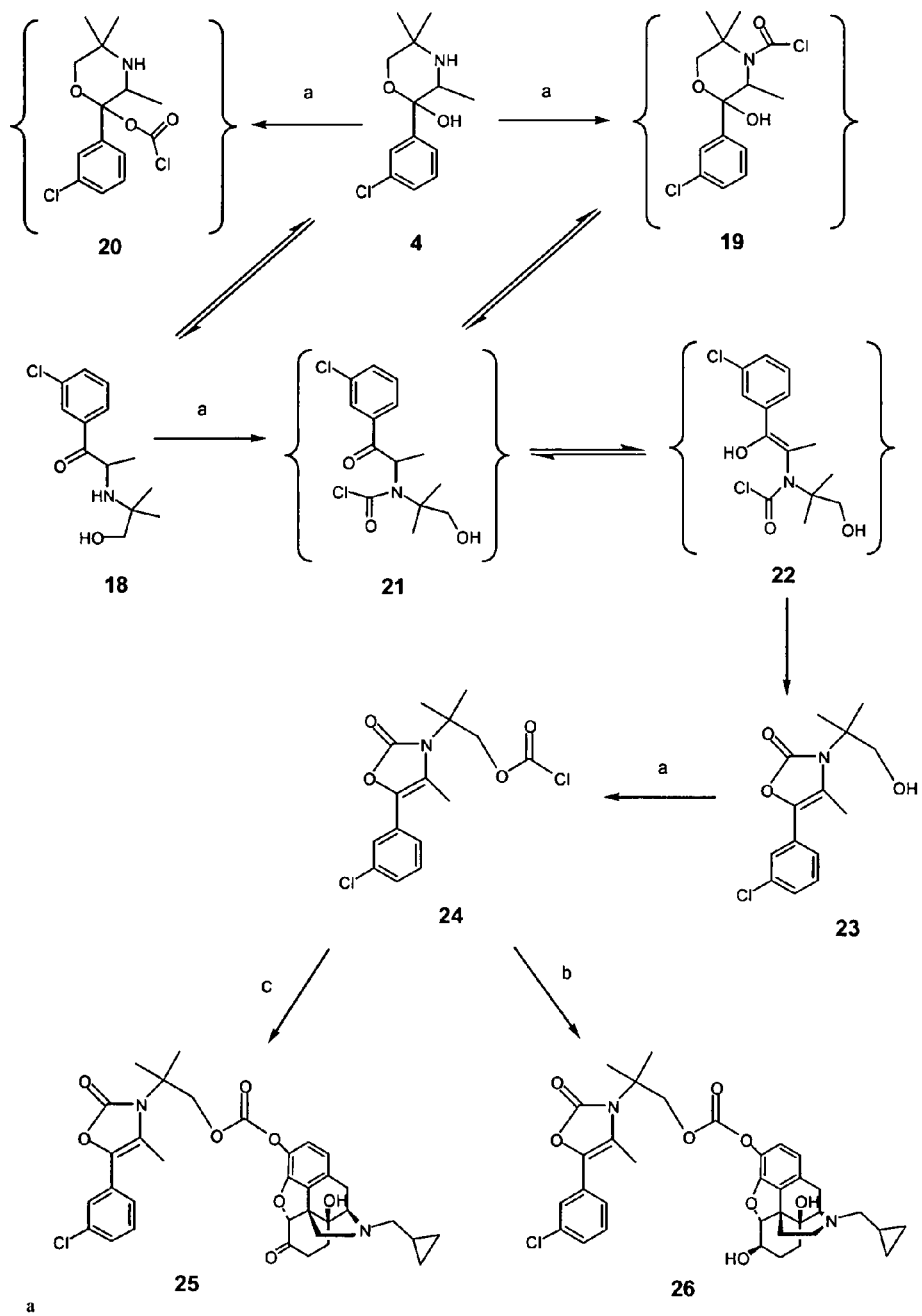

Efforts to synthesize codrugs 14-17 (FIG. 2) of BUPOH with NTX or NTXOL were also explored. The hemiketal form of BUPOH, 4, exists in equilibrium with its uncyclized form, 18 (FIG. 5). Thus, if the hemiketal form of BUPOH, 4, is reacted with phosgene, then either the chlorocarbamate intermediate 19 (FIG. 5), the chlorocarbonate intermediate 20 (FIG. 5), or both, could be formed, either of which if coupled with NTX or NTXOL would afford codrugs 14-17 (FIG. 2). Also, there is a possibility that the formation of 19 might be followed by ring opening, leading to the formation of 21 (FIG. 5). On the other hand, if the ring-open form of BUPOH, 18, reacts with phosgene, the chlorocarbamate intermediate, 21, would be expected to be formed. If 21 is stable enough to couple to NTX or NTXOL, it may undergo subsequent cyclization to the hemiketal form, resulting in the formation of codrugs 14-17. Also, BUPOH may be initially N-chlorocarbonylated to afford 21, which, like the corresponding BUP analog, 6, can exist in equilibrium with its enol tautomer, 22 (FIG. 5), followed by rapid intramolecular O-acylation to 23 (FIG. 5). When equimolar amounts of BUPOH and phosgene were reacted under basic conditions, the phosgene-BUPOH intermediate 23 (FIG. 5) was formed as the major product in the reaction. Compound 23 could be isolated, purified and fully characterized.

These results clearly indicate that the ring opened and cyclized (hemiketal) forms of BUPOH are in dynamic equilibrium under the conditions of the initial acylation reaction with phosgene (FIG. 5), although the possibility that 22 might be formed by ring opening of 19, if it is formed, cannot be excluded. Unlike the corresponding BUP analog, 9, intermediate 23 has a terminal hydroxyl group that can be utilized for linking with NTX or NTXOL via a carbonate moiety. Furthermore, the cyclic carbonate analog of BUPOH, 23, is expected to be enzymatically cleaved to BUPOH in vivo. Thus, this modified BUPOH entity was considered to be a valid substitute for BUPOH in BUPOH-NTX or BUPOH-NTXOL codrug molecules. Also, when BUPOH was reacted with excess phosgene under basic conditions, the intermediate 24 (FIG. 5) was the major product in the reaction. Intermediate 24 could be isolated and fully characterized, and afforded the modified codrug 25 (FIG. 5) on treatment with NTX in dichloromethane.

In a similar manner, the desired NTXOL-BUPOH codrug 26 (FIG. 5) was obtained when compound 24 was reacted with NTXOL in dichloromethane in the presence of triethylamine. These results again indicate that the ring opened and cyclized (hemiketal) forms of BUPOH are in dynamic equilibrium under the conditions of the initial N-chlorocarbonylation reaction with phosgene (FIG. 5).

Hydrolysis Studies on Codrugs 25 and 26.

Any drug that is to be formulated into a dosage form must exhibit stability in the medium that it is formulated in. On the other hand, the BUPOH-NTX/NTXOL codrugs must be capable of reverting back to the parent drugs in the body by enzymatic or chemical action. The reconversion rate must be adequate in order to deliver the active drugs effectively. In this respect, neither a codrug that degrades in its vehicle nor one that never reverts to the parent drugs has any therapeutic value. A codrug that does not have enough chemical stability to withstand the rigors of transport across the stratum corneum is equally worthless.

Figure 6:
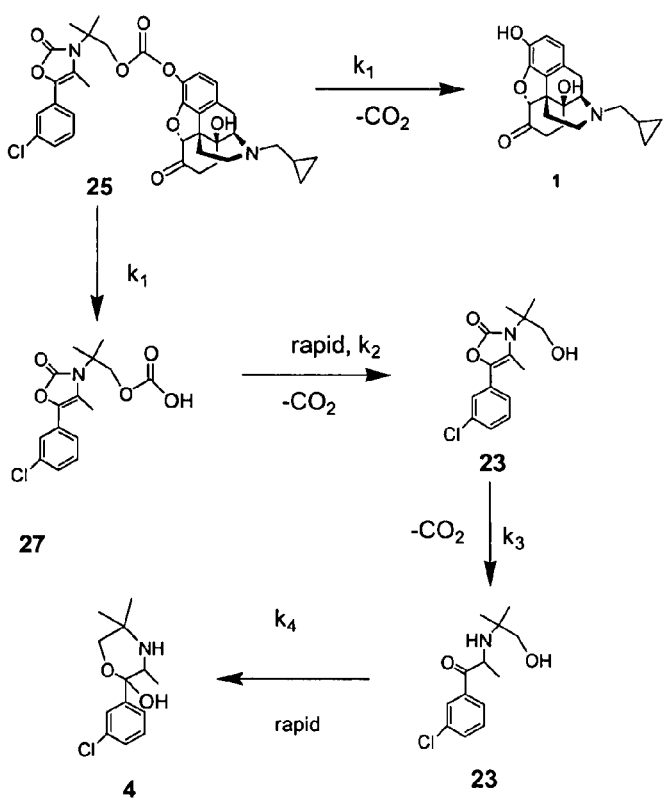

Although it is considered that codrugs 25 and 26 are likely to be cleaved enzymatically in vivo to generate BUPOH and NTX and BUPOH and NTXOL, respectively, initial studies on the hydrolysis of these codrugs in buffer at physiological pH should provide good evidence that the parent drugs will be efficiently formed. To determine whether codrugs 25 and 26 could be hydrolyzed to the parent drugs, hydrolysis studies were carried out at physiological (pH 7.4) using isotonic phosphate buffer. Skin has been shown to be a metabolically active organ for NTX carbonate prodrugs. (Pillai, et al., *Pharm. Res.* 2004, 21, 1146-1152). Thus, these carbonate codrug molecules should also be susceptible to hydrolytic cleavage, and we anticipated the hydrolytic conversion to proceed as illustrated in FIG. 6.

Figure 7:
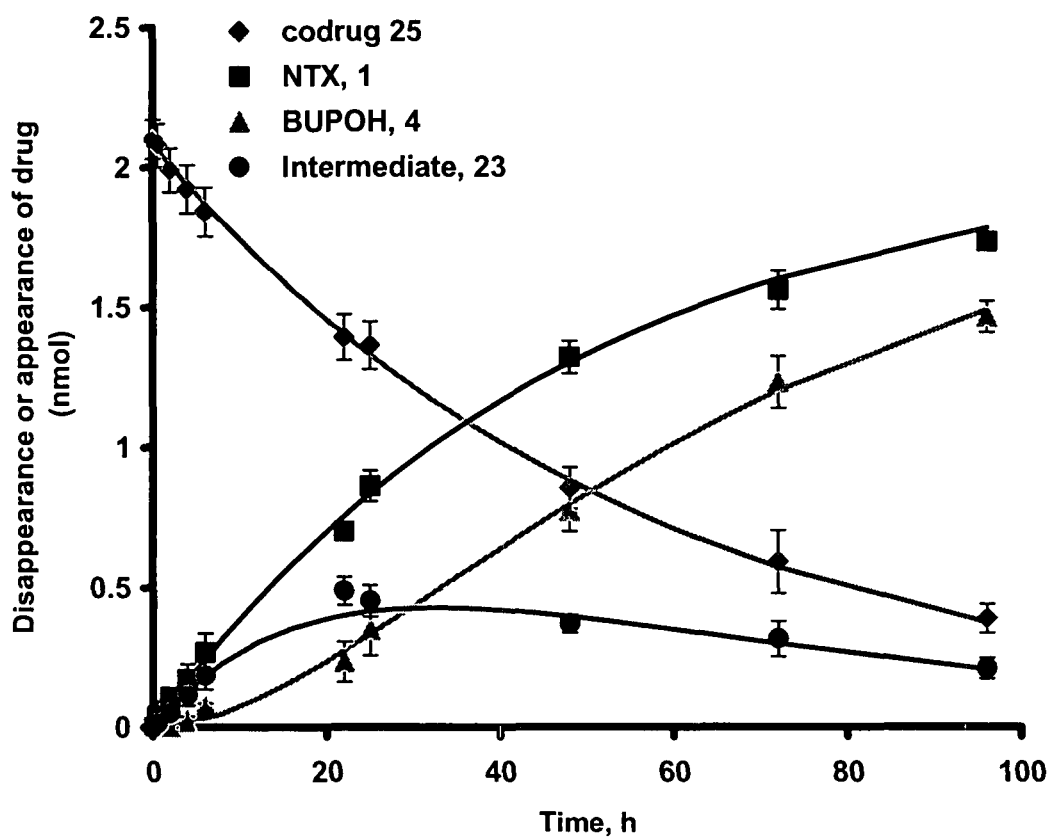
FIG. 7 shows a hydrolytic profile of the carbonate codrug (25) showing the hydrolysis into NTX and BUPOH in isotonic phosphate buffer pH 7.4 at 32° C.

The chemical stability of the codrug 25 in isotonic phosphate buffer at pH 7.4 was studied over 4 days. Concentration versus time curves for the appearance of the parent drugs NTX and BUPOH, and the disappearance of the carbonate codrug 25 are shown in FIG. 7. The first-order rate constants $k_1$ and $k_3$ were calculated to be 0.0179 $hr^{-1}$ and 0.0483 $hr^{-1}$, respectively, for generation of NTX and BUPOH.

Similarly, hydrolytic studies with codrug 26 were also carried out, and the corresponding rate constants $k_1$, and $k_2$ were calculated to be 0.0240±0.0007 $hr^{-1}$ and 0.0139±0.0006 $hr^{-1}$, respectively. Thus, both codrugs 25 and 26 appear to hydrolyze rapidly at the carbonate linker moiety to afford NTX or NTXOL followed by hydrolytic cleavage of the resulting cyclic BUPOH intermediate 23, to generate BUPOH.

The Physicochemical Properties of the Codrugs.

A more qualitative basis for the design of codrugs to enhance transdermal delivery of NTX or NTXOL is to improve the physicochemical properties essential for increased permeation through skin. Some of the physicochemical properties of codrugs 25 and 26 were measured and compared to those for NTX or NTXOL, and these are shown in Table 1.

TABLE 1

Physicochemical properties of NTX, NTXOL, and the carbonate codrugs 25 and 26.

| Compound | MW | MP (° C.) | clog P‡ | Half-life, $t_{1/2}$ (hrs)* |
|---|---|---|---|---|
| 1 | 341.40 | 175.7 ± 1.20 | 0.36 | stable |
| 2 | 343.42 | 187.76 ± 2.62 | 0.83 | stable |
| 4 | 255.74 | 124.40 ± 1.60 | 2.87 | stable |
| 25 | 649.13 | 137.00 ± 1.41 | 3.23 | 36.68 ± 2.88 |
| 26 | 651.15 | 159.50 ± 2.12 | 3.71 | 28.88 ± 2.82 |

‡Derived from Daylight ® Software
*Studied in isotonic phosphate buffer, pH 7.4 at 32° C.

The melting points of the codrugs were measured because. This physical property can be easily related to the drug solubility properties. (Stinchcomb, et al., *Pharm. Res.* 1995, 2, 1526-1529; Jain, et al., J. Pharm. Sci. 2001, 90, 234-252). As shown in Table 1, the calculated clog P values were found to be higher for the codrugs compared to those for the corresponding parent drugs. The clog P value provides a way of estimating the lipophilicity of a drug, and the higher the clog P value the more lipophilic the drug. Increased lipophilicity of a transdermal drug causes an increase in skin permeability and is primarily attributed to an increase in the partitioning of the drug into the skin. Another important physicochemical property necessary for enhancement of transdermal delivery is rapid bioconversion of the codrug to the corresponding parent drugs. Rapid bioconversion rates of codrugs are represented by short half-lives in isotonic phosphate buffer (pH 7.4/32° C.), and these values can be significantly increased in vivo, because in addition to hydrolysis, the codrugs are also susceptible to enzymatic action by esterases. In addition to regeneration of the active parent drugs, rapid bioconversion of the codrugs in the skin causes an enhancement of the concentration gradient across skin, and consequently leads to an increased potential of the drug to cross the skin barrier.

1.3 Conclusions

Two novel codrugs of NTX and NTXOL with BUPOH have been synthesized, and the kinetics of their hydrolysis also studied. The physicochemical properties of these 25 and 26 codrugs indicate that both codrugs have the capability to permeate the skin at a higher rate when compared to either NTX or NTXOL. Both codrugs were hydrolyzed in isotonic phosphate buffer (pH 7.4/32° C.) and efficiently released the parent drugs. Thus, the two codrugs 25 and 26 are predicted to be cleaved enzymatically in vivo to generate BUPOH and NTX, and BUPOH and NTXOL, respectively, representing potential candidates for transdermal delivery of these drug entities for the treatment of both alcohol abuse and tobacco dependency.

1.4 Experimental Section

Chemistry

All purchased solvents and reagents were used without further purification. Phosgene was purchased from Fluka Chemie AS. (Note!!! Care must be exercised in the handling of phosgene). Flash column chromatography was carried out using ICN SilicTech 32-63, 60 Å silica gel. TLC analyses were carried out on EMD Chemicals Inc. glass plates pre-coated with 250 μm silica gel 60 $F_{254}$. Melting points were determined on a Fisher Scientific melting point apparatus and are uncorrected. $^1$H and $^{13}$C NMR spectrometric analyses were recorded on a Varian spectrometer, operating at 400.1 and 299.9 MHz, respectively. Chemical shifts are reported in parts per million (δ) using TMS as the internal standard. The splitting pattern abbreviations are as follows: s=singlet, d=doublet, t=triplet, q=quartet, br=broad. Mass spectra were recorded on a JEOL JMS-700T MStation or on a Bruker Autoflex MALDI-TOF MS. GC-mass spectra were recorded on an Agilent 6890 GC incorporating an Agilent 7683 autosampler and an Agilent 5973 MSD.

Liquid Chromatography—Mass Spectrometry Identification of Synthetic Products

Chromatography was performed on a WATERS SYMMETRY® C18 (2.1 mm×150 mm, 5 μm) column at 35° C. using a mobile phase consisting of acetonitrile: 2 mM ammonium acetate (32:68 v/v for NTX, NTXOL, BUP and BUPOH; 80:20 v/v for 22 and 23; and 60:40 v/v for 13 and a flow rate of 0.25 mL/min. WATERS SYMMETRY® C18 (2.1 mm×10 mm, 3.5 μm) guard column was also used. The LC-MS system consisted of a WATERS ALLIANCE 2695 HPLC pump (Waters, Milford, Mass., USA), a WATERS ALLIANCE 2690 autosampler, and a MICROMASS ZQ detector (Waters, Milford, Mass., USA) using electrospray ionization (ESI) for ion production. Selected ion monitoring (SIM) was performed in the positive mode, with dwell time set at 0.30s. Capillary voltage was 4.5 kV and cone voltage was 30 V. The source block and desolvation temperatures were 120 and 250° C., respectively. Nitrogen was used as a nebulization and drying gas at flow rates of 50 and 450 L/h, respectively. LC/MS data are as follows, for NTX m/z 342 ($M^+$, retention time: 4.80 min), NTXOL m/z 344 ($M^+$, retention time: 3.22 min), 22 m/z 650 ($M^+$, retention time: 3.51 min), 24 m/z 282 ($M^+$, retention time: 3.13 min), and 23 m/z 652 ($M^+$, retention time: 4.21 min).

Synthesis of 6 β-naltrexol (2).

NTXOL base was synthesized by a modification of a previously published method. (Chatterjie, et al., J. Med. Chem. 1975, 18(5), 490-492). To a suspension of NTX free base (10.22 g, 30.0 mmol) under argon was added 100 mL (enough to afford complete solution) of 7.22 M aqueous NaOH. The alkaline dissolution of NTX was treated dropwise at ambient temperature over 20 min with 13.0 g (120 mmol) of formamidinesulfinic acid dissolved in 200 mL of 7.22M aqueous NaOH. After the addition was complete, the solution was heated and stirred at 80-85° C. for 1.5 h when silica gel TLC analysis indicated that the reaction was complete. The reaction mixture was cooled (ice bath) and then treated dropwise under argon with a solution of ammonium chloride (15.40 g, 288 mmol) in distilled water (100 mL). The aqueous mixture was extracted with 5×100 mL of $CHCl_3$, the combined organic extracts were filtered through a pad of $Na_2SO_4$ and evaporated in vacuum to afford the crude product (free base) as foam, which was dissolved in 20 mL of warm (50° C.) ethyl acetate and diluted to 60 mL with warm n-hexane. Crystallization occurred spontaneously on cooling. The crystals were collected by filtration, washed with 2×10 mL of cold ethyl acetate/n-hexane (1:3 volume/volume), and oven-dried in vacuum at 60° C. to give 9.12 g (89% yield) of NTXOL as a white solid, m.p. 175-177° C. (lit. (Perrine, et al., Journal of Chemical Education 2000, 77(11), 1479-1480) m.p. 188-190° C.). The NMR spectral data were consistent with the previous published data. (Rukstalis, et al., Clin. Exp. Res. 2000, 24(10), 1593-1596). $^1$H NMR ($CDCl_3$, 400 MHz): δ 6 6.71 (d, J=8.1 Hz, 1 H), 6.56 (d, J=8.1 Hz, 1 H), 4.55 (d, J=6.1 Hz, 1 H), 3.57 (m, 1 H), 3.16-3.02 (m, 2H), 2.70-2.58 (m, 2H), 2.37 (d, j=6.4 Hz, 2H), 2.33-2.22 (m, 1H), 2.16-2.06 (m, 1H), 2.02-1.88 (m, 1H), 1.72-1.55 (m, 2H), 1.54-1.44 (m, 1H), 1.38-1.24 (m, 1H), 0.82 (m, 1H), 0.60-0.50 (m, 2H), 0.20-0.10 (m, 2H) ppm. $^{13}$C NMR (dmso-d6, 300 MHz): δ 142.5, 140.5, 132.0, 123.1, 118.1, 117.0, 95.4, 71.7, 69.7, 61.8, 58.5, 46.9, 43.6, 30.4, 29.7, 27.3, 22.2, 9.3, 3.8, 3.6 ppm. LC/MS m/z 344 ($M^+$) single peak at Rt=3.22 min. m.p.

Synthesis of Bupropion Hydrochloride

Bupropion was synthesized by a modification of a previously published method. (Perrine, et al., Journal of Chemical Education 2000, 77(11), 1479-1480). 12.24 g (72.6 mmole) of m-chloropropiophenone, was dissolved in 25.0 ml of methylene chloride in a 50-ml round-bottom flask. A few drops of 1.0 M solution of $Br_2$ in methylene chloride were added with stirring and the reaction was briefly warmed to initiate the reaction (as judged by the disappearance of the color of the bromine). Then, the flask was placed in an ice bath and 11.6 g (72.5 mmol) of the bromine in methylene chloride solution was added drop-wise with stirring. The methylene chloride was removed by distillation. 35 ml of t-butylamine and 25 ml of NMP were added, and the flask was heated in a 50-60° C. water bath with stirring for 10 min. Then, the contents of the flask were transferred to a separatory funnel, of 100 ml of 10% aqueous sodium carbonate was added, and the mixture was extracted with ether (3×50 ml). The combined ether extracts were washed with water (3×50 ml), then brine solution (50 ml), dried over anhydrous $K_2CO_3$, and transferred to a beaker chilled in an ice bath. A 20:100 v/v mixture of concentrated HCl and isopropyl alcohol was added drop-wise with stirring until the contents are acidic. The desired product was filtered at the pump, washed with ether, and dried to afford BUP. HCl as a white solid (20.1 g, 95% yield), m.p. 236-238° C. (lit. (Mehta, U.S. Pat. No. 3,819,706) m.p. 233-234° C.). $^1$H NMR (DMSO-$d_6$, 400 MHz): δ 9.75 (d, J=12.3 Hz, 1H), 8.63 (br, 1H), 8.27 (s, 1H), 8.17 (d, J=7.8 Hz, 1H), 7.85 (d, J=7.8 Hz, 1H), 7.69 (d, $J_1$=7.8 Hz, $J_2$=7.8 Hz, 1H), 5.32 (qt, J=7.2 Hz, 1H), 1.53 (m, J=7.2 Hz, 3H), 1.32 (s, 9H) ppm. $^{13}$C NMR (DMSO-$d_6$, 300 MHz): δ 203.60, 136.56, 133.83, 132.94, 130.70, 127.87, 126.98, 52.10, 50.31, 29.39, 22.18 ppm.

Synthesis of Bupropion Free Base (2).

1.0 g of bupropion hydrochloride salt was dissolved in the minimum amount of water in 250 ml flask. The contents of the flask were transferred to a separatory funnel, to which 20 ml of 10% aqueous sodium carbonate was added, and the mixture was extracted with methylene chloride (3×50 ml). The combined methylene chloride extracts were washed with water (3×50 ml), then brine solution (50 ml), dried over anhydrous $K_2CO_3$, filtered and the filtrate stripped down under reduced pressure on a rotary evaporator to give the desired product as a yellow oil (7.9 g, 90% yield). $^1$H NMR ($CDCl_3$, 400 MHz): δ 7.90 (s, 1H), 7.81 (d, j=7.8 Hz, 1H), 7.48 (d, j=7.8 Hz, 1H), 7.37 (dd, $j_1$=$j_2$=7.8 Hz, 1H), 4.24 (qt, J=7.2 Hz, 1H), 1.19 (d, j=7.2 Hz, 3H), 0.97 (s, 9H) ppm. ppm; MS m/z 240 ($M^+$). LC-MS m/z 240 ($M^+$) single peak at Rt=8.40 min.

Synthesis of Hydroxybupropion (4).

The racemate (Morgan, et al., U.S. Patent Appl. Publ. 2003/0064988) of hydroxybupropion [(+/−)-2-(3-chlorophenyl)-3,5,5-trimethyl-2-morpholinol] was synthesized by the following procedure. 10.2 g (60.5 mmole) of m-chloropropiophenone was dissolved in 25.0 ml of methylene chloride in a 50-ml round-bottom flask. A few drops of 1.0 M solution of $Br_2$ in methylene chloride were added with stirring and the reaction was briefly warmed to initiate the reaction (as judged by the disappearance of the color of the bromine). Then, the flask was placed in an ice bath and 11.6 g (72.5 mmol) of the bromine in methylene chloride was added drop-wise with stirring. The methylene chloride was removed by distillation. 40 ml of 2-amino-2-methyl-1-propanol and 25 ml of NMP were added, and the flask was heated in a 50-60° C. water bath with stirring for 50 min. Then, the contents of the flask were transferred to a separatory funnel, 100 ml of 10% aqueous sodium carbonate was added, and the mixture was extracted with methylene chloride (3×50 ml). The combined methylene chloride extracts were washed with water (3×50 ml), then brine solution (50 ml), dried over anhydrous $K_2CO_3$, and reduced to a small volume under reduced pressure on a rotary evaporator. The desired product was precipitated by trituration with excess pentane. The resulting solid was filtered at the pump, and further purified by recrystallization from methylene chloride and pentane mixture to afford BUPOH as a white solid (17.3 g, 92% yield), m.p. 123-126° C. $^1$H NMR (CDCl$_3$, 300 MHz): δ 7.58 (s, 1H), 7.44 (m, 1H), 7.27-7.25 (m, 2H), 3.76 (d, j=11.1 Hz, 1H), 3.36 (d, j=11.1 Hz, 1H), 3.12 (q, j=6.6 Hz, 1H), 1.34 (s, 3H), 1.01 (s, 9H), 0.77 (d, j=6.6 Hz, 3H) ppm. ppm; MS m/z 256 (M$^+$). LC-MS m/z 256 (M$^+$), single peak at Rt=3.96 min.

Synthesis of 3-tert-Butyl-5-(3-chloro-phenyl)-4-methyl-oxazolidin-2-one (9).

A solution of phosgene (20% w/w in toluene, 10.0 ml, 20.0 mmol) was cooled to 0° C. in an ice-bath under argon. To this stirred solution was added a mixture of BUP (1.0 g, 4.2 mmol) and triethylamine (1.7 ml, 12.5 mmol) in 20.0 ml of methylene chloride. After stirring for 48 h, the excess phosgene and solvents were removed in a stream of argon. The resulting residue was dissolved in methylene chloride and washed with 5% hydrochloric acid ((2×60 ml), water (50 ml), and then brine solution (20 ml). The organic phase was then separated and dried over anhydrous sodium sulfate, filtered and the solvent stripped off under reduced pressure and dried to afford 9 as a brown oil (1.1 g, 90% yield). $^1$H NMR (CDCl$_3$, 300 MHz): δ 7.46-7.28 (m, 4H), 2.39 (s, 3H), 1.68 (s, 9H) ppm. $^{13}$C NMR (CDCl$_3$, 300 MHz) δ: 154.3, 134.7, 133.9, 130.2, 130.0, 127.9, 126.6, 124.7, 121.1, 58.7, 29.8, 14.0 ppm. LC-MS m/z 265 (M), single peak at Rt=3.12 min.

Synthesis of Naltrexol Duplex Codrug (13).

A solution of 1.6 ml of phosgene (3.0 mmole, 20% w/w in toluene) was cooled to 0° C. in an ice-bath under argon. To this stirred solution a mixture of NTXOL (120 mg, 0.35 mmol) and triethylamine (50 μl, 0.36 mmol) in 20.0 ml of methylene chloride was added. After stirring for 20 h, the excess phosgene and solvents were removed in a stream of argon. The resulting residue was dissolved in methylene chloride and washed with water (2×50 ml), 10% aqueous sodium carbonate (2×40 ml), then brine solution (50 ml). The organic phase was then separated and dried over anhydrous sodium sulfate, filtered, and the filtrate reduced to a small volume under reduced pressure on a rotary evaporator. The desired product was precipitated by trituration with excess pentane. The resulting solid was filtered at the pump, and further purified by recrystallization from a mixture of methylene chloride and pentane to afford 13 as a white solid (102 mg, 82%). $^1$H NMR (CDCl$_3$, 400 MHz): δ 6.97 (d, J=8.0 Hz, 1H), 6.68 (d, J=8.0 Hz, 1H), 4.58 (d, J=6.0 Hz, 1H), 3.62-3.50 (m, 1H), 3.16-3.02 (m, 2H), 2.70-2.58 (m, 2H), 2.37 (d, j=6.4 Hz, 2H), 2.33-2.22 (m, 1H), 2.16-2.06 (m, 1H), 2.02-1.88 (m, 1H), 1.72-1.55 (m, 2H), 1.54-1.44 (m, 1H), 1.38-1.24 (m, 1H), 0.82 (m, 1H), 0.60-0.50 (m, 2H), 0.20-0.10 (m, 2H) ppm. $^{13}$C NMR (CDCl$_3$, 300 MHz): δ 150.79, 146.87, 134.18, 133.61, 131.51, 121.68, 119.12, 97.56, 72.42, 70.27, 62.08, 59.39, 47.40, 43.75, 30.82, 29.70, 25.38, 23.16, 9.55, 4.14, 3.98 ppm. LC-MS m/z 713 (M$^+$), single peak at Rt=18.15 min.

Synthesis of Hydroxybupropion Phosgene Intermediate 24 [5-(3-Chloro-phenyl)-3-(2-chlorocarboinoic-1,1-dimethyl-ethyl)-4-methyl-oxazolidin-2-one]

A solution of phosgene, (20% w/w in toluene, 15 ml) was cooled to 0° C. in an ice-bath under argon. To this stirred solution was added a mixture of BUPOH (2.00 g, 7.84 mmol) and triethylamine (3.3 ml, 24 mmol) in 20.0 ml of methylene chloride. After stirring for 48 h, the excess phosgene and solvents were removed in a stream of argon. The resulting residue was dissolved in methylene chloride and washed with water (2×50 ml), and then brine solution (20 ml). Then the organic phase was separated and dried over anhydrous sodium sulfate, filtered and the filtrate reduced to a small volume and dried under reduced pressure to afford 23 as yellow oil (2.4 g, 90% yield). $^1$H NMR (CDCl$_3$, 300 MHz): δ 7.38-7.28 (m, 4H), 4.65 (s, 2H), 2.34 (s, 3H), 2.24 (m, 1H), 1.75 (s, 6H) ppm.

Synthesis of Hydroxybupropion: Naltrexone Codrug (25)

A solution of 24 1.02 g, 2.97 mmol) in methylene chloride (20 ml) was cooled to 0° C. in an ice-bath under argon. To this stirred solution was added a mixture of NTX (1.0 g, 2.93 mmol) and triethylamine (0.45 ml, 3.23 mmol) in 20.0 ml of methylene chloride. After stirring for 48 h, the reaction mixture was washed with water (2×50 ml), then brine solution (20 ml). Then the organic phase was separated and dried over anhydrous sodium sulfate and reduced to a small volume under reduced pressure. The desired product was precipitated by adding excess pentane, filtered at the pump and washed with cold pentane. The desired product was further purified by recrystallization from methylene chloride and pentane mixture to afford 25 as a white solid (1.5 g, 78% yield), m.p. 136-138° C. $^1$H NMR (CDCl$_3$, 300 MHz): δ 7.38-7.28 (m, 4H), 6.87 (d, J=8.4 Hz, 1H), 6.64 (d, J=8.4 Hz, 1H), 4.65 (s, 2H), 4.59 (s, 1H), 3.19 (d, j=6.0 Hz, 1IH), 3.13-2.92 (m, 2H), 2.68 (dd, J=5.7, 12.3 Hz, 1H), 2.59 (dd, J=6.0, 18.9 Hz, 1H), 2.50-2.34 (m, 6H), 2.24 (m, 1H), 2.09 (m, 1H), 1.85 (m, 1H), 1.75 (s, 6H), 1.60 (m, 1H), 1.52 (m, 1H), 0.89 (m, 1H), 0.60-0.52 (m, 2H), 0.20-0.11 (m, 2H) ppm. $^{13}$C NMR (CDCl$_3$, 300 MHz): δ 207.24, 153.96, 152.60, 147.42, 134.55, 134.04, 133.04, 130.35, 129.92, 129.86, 127.88, 126.68, 126.66, 124.79, 122.62, 121.69, 119.54, 90.85, 72.31, 70.18, 61.96, 60.33, 59.31, 50.75, 46.06, 36.24, 31.46, 30.71, 25.48, 25.36, 22.63, 14.38, 8.97, 4.54, 4.15 ppm. LC-MS m/z 650 (M$^+$), single peak at Rt=3.51 min.

Synthesis of Hydroxybupropion: Naltrexol Codrug (26)

A solution of 24 (1.00 g, 2.91 mmol) in methylene chloride (20 ml) was cooled to 0° C. in an ice-bath under argon. To this stirred solution was added a mixture NTXOL (1.0 g, 2.92 mmol) and triethylamine (4.5 ml, 3.23 mmol) in 20.0 ml of methylene chloride. After stirring for 48 h, the reaction mixture was washed with water (2×50 ml), then brine solution (20 ml). Then the organic phase was separated and dried over anhydrous sodium sulfate and reduced to a small volume under reduced pressure. The desired product was precipitated by adding excess pentane, filtered at the pump and washed with cold pentane. The desired product was further purified by recrystallization from methylene chloride and pentane mixture to afford 26 as a white solid (1.6 g, 85% yield), m.p. 157-161° C. $^1$H NMR (CDCl$_3$, 300 MHz): δ 7.45-7.28 (m, 4H), 6.85 (d, J=8.2 Hz, 1H), 6.65 (d, J=8.1 Hz, 1H), 4.83 (d, J=11.1 Hz, 1H), 4.54 (d, J=11.1 Hz, 1H), 4.48 (d, J=5.1 Hz, 1H), 3.58-3.42 (m, H), 3.19 (d, j=5.4 Hz, 1H), 3.16-2.92 (m, 2H), 2.70-2.52 (m, 2H), 2.28-2.20 (m, 2H), 2.18-1.80 (m, 2H), 1.77 (s, 3H), 1.75 (s, 3H), 1.48-1.39 (m, 2H), 1.37-1.20

(m, 2H), 0.82 (m, 1H), 0.60-0.50 (m, 2H), 0.20-0.10 (m, 2H) ppm. $^{13}$C NMR (CDCl$_3$, 300 MHz): δ 154.15, 152.74, 147.14, 134.66, 134.32, 133.88, 133.24, 131.14, 129.98, 129.87, 128.10, 126.78, 124.91, 121.83, 121.48, 118.90, 97.15, 72.46, 72.17, 70.23, 62.24, 60.33, 59.50, 47.24, 43.95, 31.24, 29.54, 25.68, 25.36, 25.30, 23.36, 14.40, 9.57, 4.35, 4.19 ppm. LC-MS m/z 652 (M$^+$), single peak at Rt=4.21 min.

Synthesis of 5-(3-chloro-phenyl)-3-(2-hydroxy-1,1-dimethyl-ethyl)-4-methyl-oxazolidin-2-one (23).

A solution of phosgene (20% w/w in toluene, 2.2 ml, 4.2 mmol) was cooled to 0° C. in an ice-bath under argon. To this stirred solution was added a mixture of BUPOH (1.07 g, 4.2 mmol) and triethylamine (1.2 ml, 8.6 mmol) in 20.0 ml of methylene chloride. After stirring for 18 h, the excess phosgene and the solvents were removed in a stream of argon. The resulting residue was dissolved in methylene chloride and washed with water (2×50 ml), then brine solution (20 ml). Then the organic phase was separated and dried over anhydrous sodium sulfate and reduced to a small volume under reduced pressure. The desired product was precipitated by adding excess pentane, filtered at the pump and washed with cold pentane to afford 0.92 g (86% yield) of 23. $^1$H NMR (CDCl$_3$, 300 MHz): δ 7.38-7.28 (m, 4H), 3.92 (s, 2H), 2.42 (s, 3H), 2.24 (m, 1H), 1.57 (s, 6H) ppm. $^{13}$C NMR (CDCl$_3$, 300 MHz): δ 154.48, 134134.91, 134.80, 130.09, 129.61, 128.21, 126.37, 124.41, 121.28, 121.28, 70.24, 62.24, 25.22, 13.47 ppm. LC-MS m/z 282 (M$^+$), single peak at Rt=3.13 min.

Hydrolysis Studies on the BUPOH:NTX and BUPOH:NTXOL Codrugs

Standards were prepared in the concentration range 100-1000 ng/mL in Hanks' buffer. Equal amounts of the each of the codrug were distributed into labeled test-tubes (20 nmol in each tube). Care was taken to ensure that the entire codrug was dissolved and the solution remained clear. Hydrolysis of the carbonate codrug (~20 nmol) was conducted in isotonic phosphate buffer pH 7.4 at 32° C. in a water-bath with continuous stirring. Since these codrugs are designed and synthesized for the development of a transdermal dosage form, hydrolysis studies were conducted at 32° C., which is equivalent to the skin's surface temperature. Samples were collected at predetermined time intervals and stored in the freezer at −20° C. until analyzed. All experiments were conducted in triplicate. An aliquot part (250 μL) of hydrolysis solutions was mixed with 750 μL of acetonitrile, vortexed for 30s, and analyzed by HPLC for the presence of codrug and the two corresponding parent drugs, as well as for the intermediate hydrolysis product, 23. Standards of codrug 25, codrug 26, naltrexone, 6-β-NTXOL, intermediate 23, and hydroxybupropion were prepared in isotonic phosphate buffer:acetonitrile (1:3, v/v) in the concentration range of 0.1-2.0 μg/mL, and these solutions were used for the generation of the respective calibration curves. Sample recoveries were >95% for all the drugs, and data were corrected for the respective extraction efficiencies. A modification of the high-pressure liquid chromatographic (HPLC) assay reported by Hussain et al[32] was used for the analysis of hydrolysis samples. The HPLC system consisted of a Waters (Milford, Mass., USA) model 717 Autosampler, two model 1525 Pumps, and a model 2487 dual wavelength UV absorbance detector with Millennium Chromatography software. A Brownlee C$_{18}$ reversed-phase Spheri-5 μm column (220×4.6 mm) connected to a C$_{18}$ reversed-phase guard column (15×3.2 mm) was utilized and detection of solutes was carried out at 215 nm. The mobile phase consisted of a mixture of acetonitrile: 0.1% trifluoroacetic acid adjusted to pH 3.0 with triethylamine (50:50, v/v). The mobile phase flow rate was 1.5 mL/min and 100 μL of hydrolysis sample was injected onto the column. The retention times for each of the analytes were 14.60 min, 10.50 min, 2.86 min, 2.28 min, 5.20 min, and 4.56 min for codrug 25, codrug 26, NTX, intermediate 23, and hydroxybupropion, respectively.

Example 2

Enhancement of Transdermal Delivery of 6-β-Naltrexol Via a Codrug Linked to Hydroxybupropion 2.1 Introduction In vitro results obtained by Porter et al. in electrically-stimulated guinea pig ileum indicated that 6-β-naltrexol was 4.5-fold and 2.8-fold more potent than naloxone and naltrexone, respectively (Porter et al., Addict. Biol. 7 (2002) 219-225). However, in vivo potency of a 6-β-naltrexol acute dose in mice was shown to be less than the other two antagonists, but the 6-β-naltrexol potency was time-dependent and provided a longer duration of action (Porter et al., Addict. Biol. 7 (2002) 219-225). In humans, NTX undergoes extensive first-pass metabolism with an oral bioavailability of 5-40% (PDR Generics. 2$^{nd}$ Ed., Medical Economics, Montvale, N.J., 1996, pp. 2229-2233) and is reduced at the 6-keto-group to this primary metabolite, 6-β-naltrexol. Following an oral dose of NTX in humans, 6-β-naltrexol is present in much higher concentrations in plasma than NTX and remains in the systemic circulation for a longer period of time due to its longer half-life of about 12 h, as compared with the 4 h half-life of NTX (Meyer et al., J. Clin. Psychiatry 45 (1984) 15-19). Results from a study in alcoholics showed a significant correlation between high plasma levels of 6-β-naltrexol and lower reported number of drinks per month (McCaul et al., Alcohol Clin. Exp Res. 24 (2000) 1385-1391).

Oral NTX therapy is associated with a number of gastrointestinal adverse effects such as abdominal pain, nausea, and vomiting, thereby limiting its clinical utility (Kranzler et al., Neuropsychopharmacology 22 (2000) 493-503). NTX is also a hepatotoxin that has the capacity to cause dose-related hepatocellular injury. This hepatoxicity limits dosage increases in those addicts who may benefit from an oral dose greater than 50 mg/day. It is unknown if the gastrointestinal side-effects and hepatic toxicities of NTX receive contributions from 6-β-naltrexol. However, investigations into the NTX biotransformation process have indicated that there is a large variability in the first-pass metabolism, with as much as four-fold differences in peak 6-β-naltrexol levels observed in subjects receiving oral NTX (Verebey et al., Clin. Pharmacol. Ther. 30 (1976) 315-328; McCaul et al., Alcohol Clin. Exp Res. 24 (2000) 1385-1391; Kranzler et al., Neuropsychopharmacology 22 (2000) 493-503).

Transdermal delivery of 6-β-naltrexol would be expected to have a less variable plasma concentration profile with more precise control over dosing, compared to the variability currently experienced with oral NTX. Furthermore, 6-β-naltrexol may be better tolerated than NTX in recovering opioid addicts due to its lesser inverse agonist activity and potential decreased withdrawal effects (Raehal et al., J Pharmacol Exp Ther 313 (2005) 1150-1162). Another major disappointment in oral NTX maintenance therapy has been the poor long-term patient compliance, and therefore NTX is only the drug of choice for highly motivated patients (O'Malley et al., Arch. Gen. Psychiatry 49 (1992) 881-887; Rothenberg et al., J Substance Abuse Treat. 23 (2002) 351-360). To address this compliance issue several depot injections of NTX are under development (O'Malley et al., Arch. Gen. Psychiatry 49 (1992) 881-887; Gooberman, U.S. Pat. No. 6,203,813 (Mar. 20, 2001)), but this relatively invasive dosage form would also require multiple visits to a health care professional for routine treatment. Alternatively, non-invasive transdermal delivery would avoid first-pass metabolism, in addition to diminishing gastrointestinal side effects associated with oral therapy. The application of a transdermal patch requires less patient motivation as opposed to surgical implantation/injection or daily oral dosing, and hence can be expected to improve patient compliance. A transdermal patch provides sustained-release of a drug for a maximum of about 1 week, whereas currently available ReVia®, the U.S. marketed 50-mg naltrexone HCl tablet, requires daily dosing in most cases.

Neither NTX nor 6-β-naltrexol have the essential physicochemical properties that would allow a therapeutic dose of the drug to cross the skin, so the current focus has been to solve this problem by designing and synthesizing codrugs which are more skin permeable.

Simultaneous treatment of alcohol dependence and tobacco addiction would be beneficial because of the high prevalence of cigarette and alcohol co-abuse. Therefore, bupropion and its major active metabolite, hydroxybupropion, were chosen for linkage to 6-β-naltrexol to form the codrug. Bupropion is used clinically as an antidepressant and in smoking cessation (Johnson et al., Nicotine Tobacco. Res. 3 (2001) 131-140), and is extensively metabolized in humans with less than 10% of a bupropion dose being excreted unchanged (Schroeder, J. Clin. Psychiatry. 44 (1983) 79-81). However, chemical synthesis procedures with bupropion gave unpredictable reaction products which were either difficult to isolate and/or too unstable. Pharmacological activity of bupropion might be due to, or receive significant contributions from, its major metabolite hydroxybupropion (Schroeder, J. Clin. Psychiatry. 44 (1983) 79-81; Belson and Kelley, J. Em. Med. 23 (2002) 223-230). Both bupropion and hydroxybupropion have better physicochemical properties that would allow for effective transdermal delivery (Scheuplein and Blank, Physiol. Rev. 51 (1971) 702-747), and this added functionality to 6-β-naltrexol via a covalent linkage can improve the permeability characteristics of 6-β-naltrexol.

Figure 8:
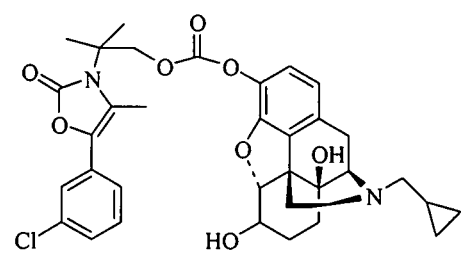
FIG. 8. shows a chemical structure of the carbonate codrug, CB-NTXOL-BUPOH, consisting of 6-β-naltrexol covalently linked to a form of hydroxybupropion.

In this study, a novel codrug consisting of 6-β-naltrexol linked to hydroxybupropion via a carbonate ester linkage was synthesized (FIG. 8). This carbonate codrug partitions into and diffuses across skin more readily, as compared to 6-β-naltrexol. Upon penetration into the skin layers, it is biotransformed into molar equivalent moieties of 6-β-naltrexol and hydroxybupropion via non-enzymatic hydrolytic cleavage and by esterase enzymes. The permeation of this codrug has been evaluated by in vitro diffusion studies with human skin to determine the level of 6-β-naltrexol transdermal delivery enhancement.

2.2. Experimental

Quantitative Analysis

A modified high-pressure liquid chromatography (HPLC) assay from Hussain et al was used for the analysis (Hussain et al., J. Pharm. Sci. 76 (1987) 356-358). The HPLC system consisted of a Waters (Milford, Mass., USA) 717 Plus Autosampler, 1525 Binary Pumps, and a 2487 dual wavelength UV absorbance detector with Breeze software. A Brownlee Valueline $C_{18}$ reversed-phase Spheri-5-μm column (220×4.6 mm) with a $C_{18}$ reversed-phase 7-μm guard column (15×3.2 mm) was used with the UV/VIS detector set at a wavelength of 215 nm. The mobile phase consisted of acetonitrile (ACN): 0.1% TFA buffer adjusted with TEA to pH 3.0 (50:50, v/v). The flow rate was 1.5 ml/min with 100 μl sample injections. Retention times in this assay were found to be 2.28, 4.56, 5.20, and 10.50 min for 6-β-naltrexol, hydroxybupropion, intermediate, and CB-NTXOL-BUPOH (the codrug), respectively. External standard solutions were analyzed with each set of diffusion samples. Standard curves exhibited excellent linearity over the entire concentration range (50-1000 ng/mL) employed in the assays. Both intraday and inter-day assays had small coefficients of variation (<10% CV) indicating that the method is reproducible, accurate, and precise. The assay sensitivity was at least 20 ng/mL or better for all the drugs.

Extraction Procedure

Diffusion samples collected in the fraction collector were processed using solid-phase extraction (Oasis MCX®, Waters Corp., Milford, Mass.). The solid-phase extraction cartridges were pretreated with 1 mL of methanol and 1 mL of distilled water. Five milliliters of diffusion receiver samples were loaded onto the cartridges. The sample-loaded cartridges were washed with 1 mL of 0.1 N HCl. Samples were eluted with 1 mL of 2% ammonium hydroxide in methanol followed by 1 mL of isopropanol, evaporated under nitrogen, reconstituted with ACN/water (1:1), sonicated for 30 s, vortexed, and placed in HPLC vials for analysis. Sample recoveries were >80% and data were corrected for the respective extraction recoveries.

Differential Scanning Calorimetry

Differential scanning calorimetry (DSC) was carried out for CB-NTXOL-BUPOH, hydroxybupropion, and 6-β-naltrexol. Heats of fusion and melting points were determined with a TA instruments 2920 DSC (New Castle, Del., USA). An accurately weighed sample of drug (2-5 mg) was sealed into the aluminium pans and thermograms were recorded at 10° C./min from ambient to 350° C. Measurements were repeated once for a total of two scans on each drug.

2.3. Solubility

The solubilities of CB-NTXOL-BUPOH, hydroxybupropion, and 6-β-naltrexol were determined by adding excess quantity of drug to mineral oil or pre-warmed HEPES-buffered Hanks' salt solution pH 7.4 at 32° C. (skin surface temperature), with equilibration while shaking in a water bath at 60 rpm. Weighing 4 mg of each of the drugs and placing them in 1 ml of each of the respective solvents was enough to ensure that there was excess drug in solution. Samples were drawn into a pre-warmed glass syringe, filtered through a syringe filter (Mineral oil: Millex FG-13, Millipore, Billerica, Mass., USA, and buffer: nylon filter, Gelman, East Hills, N.Y., USA), and measured with respect to volume and diluted with an appropriate volume of acetonitrile or buffer. The drug from the buffer samples was immediately extracted by solid phase extraction as described above. Drugs in mineral oil were diluted with a hundred-fold volume of acetonitrile and extraction recoveries were >95% for all the drugs. The sampling procedure was done in triplicate, discarding the first 40% of the initial filtrate. All samples were analyzed by HPLC. Equilibration time for the solubility studies was 48 h in mineral oil. For buffer solubilities, samples were taken after 30 min of sonication (to minimize the hydrolysis of the codrug). No significant difference was found between 30 min sonication solubility measurements and equilibrium solubility measurements taken after 48 h for 6-β-naltrexol. Solubilities were reported as mean±S.D and were statistically compared using a paired Student's t-test. Mean values were considered significantly different at p<0.05.

In Vitro Skin Diffusion Studies

Human skin harvested during abdominal reduction surgery was used for the diffusion studies. Skin sections were obtained by using a Padgett dermatome set to 250 μm; these sections were stored at −20° C. Stored skin samples were thawed to room temperature at the time of the experiment. A PermeGear flow-through (In-Line, Riegelsville, Pa., USA)

diffusion cell system was used for the skin permeation studies. Skin surface temperature was maintained at 32° C. with a circulating water bath. Data was collected by using human skin from a single donor with three cells of 6-β-naltrexol and four cells CB-NTXOL-BUPOH. Because of normal human skin inter-subject permeation variability, the codrug was compared against 6-β-naltrexol permeation within each individual skin sample. These studies were repeated three times with skin from different human subject donors. The receiver solution was HEPES-buffered Hanks' balanced salt solution pH 7.4 set at a flow rate of 1.1 ml/h. These diffusion study conditions were chosen in order to maintain tissue viability according to previous studies by Collier et al. (Collier et al., Toxicol. Appl. Pharmacol. 99 (1989) 522-533). A saturated solution of 6-β-naltrexol or CB-NTXOL-BUPOH in light mineral oil was applied to the skin in order to maintain a maximum and constant thermodynamic activity of the drug. Each cell was charged with 0.25 ml of the respective drug solution. Samples were collected in 6-h increments for 48 h. All samples were immediately processed by solid phase extraction, evaporated under nitrogen, reconstituted, and analyzed for drug content by HPLC. The human tissue use was approved by the University of Kentucky Institutional Review Board.

Cumulative quantity of drug collected in the receiver compartment was plotted as a function of time. The flux value for a given experiment was obtained from the slope of the steady-state portion of the cumulative amount of drug permeated vs. time plot. Apparent permeability coefficient values were computed from Fick's First Law of diffusion:

$$\frac{1}{A}\left(\frac{dm}{dt}\right) = J_S = K_P \Delta C \tag{1}$$

In Eq. (1), $J_s$ is the steady-state flux, M is the cumulative amount of drug permeating the skin, A is the area of the skin (0.95 cm$^2$), $K_P$ is the effective permeability coefficient in cm/h, and $\Delta C$ is the difference in concentrations of the drugs between the donor and receiver compartments. Sink conditions were maintained in the receiver throughout the experiment, so $\Delta C$ was approximated by the drug concentration (solubility in this case) in the donor compartment.

The concentration of the drugs in the skin was determined after the 48-h experiment. The skin tissue was rinsed with filtered water and blotted with a paper towel. The tissue was tape-stripped twice to remove surface formulation. The area of skin with drug contact was cut out, chopped into tiny pieces, and placed in a pre-weighed vial. The vial was weighed to calculate the mass of the skin. Ten milliliters of acetonitrile was added to each vial, the vials vortexed, sonicated for 10 min, and placed in a shaker overnight. The following day, a 1 ml sample was obtained from the vials and placed in autosampler vials for analysis. The skin concentration results were reported as micromoles of drug per gram of wet tissue weight. Flux values and skin concentrations for each of the drugs were reported as mean±S.D and were statistically compared using a paired Student's t-test. Flux enhancement as well as drug disposition in the skin were considered significant at p<0.05.

Transepidermal water loss (TEWL) was measured before and after treating the skin with the drug solutions in order to determine the barrier integrity of the skin. The principal homeostatic function of the human stratum corneum (SC) is to restrict the loss of water to the external environment, with typical basal values of TEWL in adults with healthy skin measuring 5-10 g·m$^{-2}$·h$^{-1}$ (Kalia et al., Pharm. Res. 17 (2000) 1148-1150). However, if the skin is damaged, there will be significant transepidermal water loss and values are expected to be much higher. Therefore, TEWL is used to check the integrity of the skin used in the experiment.

Chemical Stability of the Codrug in Buffer

Figure 10:
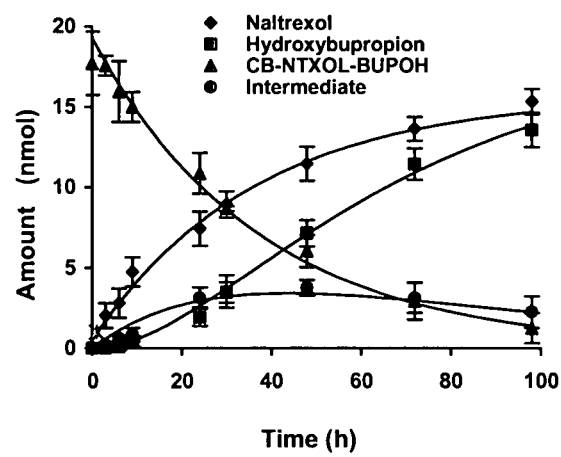
FIG. 10. shows a hydrolysis profile of the carbonate codrug, CB-NTXOL-BUPOH, regenerating into 6-β-naltrexol and hydroxybupropion in isotonic phosphate buffer pH 7.4 at 32° C. Solid lines represent predicted profiles of the drugs with time and data is represented as mean±s.d.

One of the prerequisites in the designing of prodrugs or codrugs is that these moieties must be capable of reverting back to the parent drugs once they cross the skin's barrier, either by enzymatic or chemical action. Extensive conversion of carbonate prodrugs has been shown to occur in the viable skin layers of the epidermis and dermis. Additionally, the conversion rates must be fast enough in order to deliver the active drugs for therapeutic effect. The carbonate codrug is susceptible to hydrolysis, and the conversion to the parent drugs proceeds as illustrated in FIG. 10.

Figure 9:
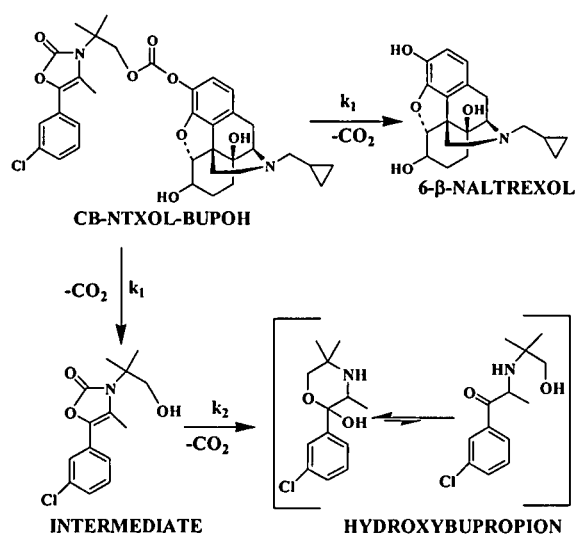
FIG. 9. is a schematic diagram illustrating the hydrolytic pathway of CB-NTXOL-BUPOH to give 6-β-naltrexol and hydroxybupropion.

The chemical stability of the codrug in HEPES-buffered Hanks' balanced salt solution pH 7.4 was studied by using sub-saturated concentrations (20 nmol/mL) of the codrug. Samples (2 ml) were distributed into sealed vials and placed at 32° C. One vial was removed immediately after starting the experiment and at predetermined time intervals for 4 days and stored at -70° C. until analysis. The sample solution (0.25 ml) was diluted with acetonitrile and analyzed by HPLC. Concentration versus time curves for the appearance of parent drugs; 6-β-naltrexol and hydroxybupropion, and the disappearance of the carbonate codrug were fitted to a mathematical model derived from FIG. 9 using nonlinear least-squares regression analysis (SCIENTIST®, Micromath Inc., Salt Lake City, Utah) to obtain estimates for the two first-order rate constants, $k_1$ and $k_2$. The following differential equations can be generated from FIG. 9:

$$\frac{d[CB\text{-}NTXOL\text{-}BUPOH]}{dt} = -k_1[CB\text{-}NTXOL\text{-}BUPOH] \tag{2}$$

$$\frac{d[NTXOL]}{dt} = k_1[CB\text{-}NTXOL\text{-}BUPOH] \tag{3}$$

$$\frac{d[INTERMEDIATE]}{dt} = k_1[CB\text{-}NTXOL\text{-}BUPOH] \tag{4}$$

$$\frac{d[BUPOH]}{dt} = k_2[INTERMEDIATE] \tag{5}$$

where [CB-NTXOL-BUPOH], [NTXOL], [INTERMEDIATE], and [BUPOH] are the concentrations of the carbonate codrug, 6-β-naltrexol, intermediate shown in FIG. 9, and hydroxybupropion, respectively at time t. First-order rate constants are described by $k_1$, and $k_2$.

Stratum Corneum/Vehicle Partition Coefficient Studies

Human epidermis with stratum corneum (SC) side facing up was incubated on filter paper soaked with 0.1% trypsin in 0.5% sodium bicarbonate solution at 37° C. for 3 h. The SC membrane was separated and dried in a vacuum dessicator. After 24 h, the SC was dipped in acetone for 20 s to remove sebaceous lipids and dried again.

Approximately 5 mg of SC was equilibrated with sub-saturated drug solutions in 0.5 g of mineral oil solution at 32° C. for 48 h. Two different levels of sub-saturated drug solutions, 10 and 20 nmol in 0.5 g of mineral oil, were used in SC/vehicle partition coefficient studies. However, irrespective of the drug concentrations used, the ratio derived should always be the same since the partition coefficient measurement is an equilibrium phenomenon. An aliquot of the mineral oil solution (10 μl) was withdrawn at the end of the study and was diluted to 1000 μl with acetonitrile. The samples were then analyzed by HPLC. The amount of the drug partitioned into the SC was measured by subtracting the amount present in the mineral oil after equilibration from the initial drug concentration in the mineral oil. The partition coefficient ratio was expressed as the concentration of the drug in 1 g of SC divided by the concentration of the drug in 1 g of mineral oil. SC/Vehicle partition coefficients for each of the drugs were reported as mean±S.D and were statistically compared using a paired Student's t-test. Partition coefficients were considered significantly different at p<0.05.

2.4. Results and Discussion

A carbonate codrug of 6-β-naltrexol linked to hydroxybupropion was designed, synthesized, and tested in order to determine the enhancement in the transdermal delivery of 6-β-naltrexol, as well as to determine the improvements in the physicochemical parameters necessary for transport across skin. Hydroxybupropion has better skin permeation physicochemical parameters as compared to 6-β-naltrexol, and this added functionality of hydroxybupropion to the 6-β-naltrexol via covalent linkage should improve the permeability characteristics of 6-β-naltrexol.

Carbonate prodrugs are hydrolyzed in vivo to the active drugs either by chemical hydrolysis or enzymatically by The melting points and heats of fusion of 6-β-naltrexol, hydroxybupropion, and CB-NTXOL-BUPOH were measured, as these properties are often easily related to drug solubilities. The carbonate codrug exhibited a significantly lower melting point as compared to 6-β-naltrexol, suggesting that the addition of the hydroxybupropion moiety to 6-β-naltrexol significantly decreased the intermolecular cohesion and crystallinity. Crystallinity has been suggested to have an inhibitory effect on the dissolution rates and solubilities of solutes (Jain et al., J. Pharm. Sci. 90 (2001) 234-252). Solubility or drug solution saturation conditions provide the maximum thermodynamic activity driving force for drug transport across the skin. Reference state thermodynamic activities were calculated from the equation in Table 2. A significantly smaller heat of fusion and a corresponding higher calculated relative thermodynamic activity were observed for CB-NTXOL-BUPOH, as compared 6-β-naltrexol. Therefore, one can predict that CB-NTXOL-BUPOH has a higher oil solubility and possibly an increased chance of crossing the intercellular lipid barrier of the stratum corneum at a faster rate than 6-β-naltrexol, if their diffusion coefficients are not substantially different and the stratum corneum is the rate-determining barrier to diffusion.

TABLE 2

Differential thermal analysis of 6-β-naltrexol, CB-NTXOL-BUPOH, and hydroxybupropion.

|  | 6-β-naltrexol | CB-NTXOL-BUPOH | Hydroxy-bupropion |
| --- | --- | --- | --- |
| Molecular weight (g mol$^{-1}$) | 343.42 | 651.15 | 255.74 |
| Melting point, $T_f$(° C., ±s.d, n = 3) | 187.76 ± 2.62 | 159.50 ± 2.12 | 124.40 ± 1.60 |
| Heat of fusion, $\Delta H_f$(kJ mol$^{-1}$, ±s.d., n = 3) | 15.05 ± 0.20 | 12.68 ± 0.08 | 10.8 ± 0.05 |
| Mean activity of solid @ T = 25° C., $a_2{}^a$ | 0.12 | 0.20 | 0.34 |

$^a$Calculated from $\ln a_2 = \frac{-\Delta H_f}{RT}\left(\frac{T_f - T}{T_f}\right)$ (from Hildebrand & Scott 1950, Stinchcomb et al 1995) [29, 30]

esterase activity. To gain more information on the chemical hydrolysis stability of CB-NTXOL-BUPOH, the drug concentration was monitored over time in isotonic phosphate buffer (pH 7.4) at 32° C. (skin's surface temperature). As shown in FIG. 10, CB-NTXOL-BUPOH was hydrolyzed into the active parent drugs. The hydrolysis data were fit to a mathematical model derived from FIG. 9 using nonlinear least-squares regression analysis (SCIENTIST®, Micromath Inc., Salt Lake City, Utah). Data analysis revealed that the codrug disappearance followed first order kinetics and that the apparent half-life was approximately 29 hours. However, the regeneration of hydroxybupropion was slower than the regeneration of 6-β-naltrexol, since it proceeded through an intermediate step. Hydroxybupropion was found to exist in equilibrium between two forms; the cyclized hemiketal form and the open form depending upon the pH conditions as shown in FIG. 9. However, under the conditions in which we conducted our studies, hydroxybupropion existed predominantly as a cyclized hemiketal form. Isolation of the intermediate was an integral part of elucidating the hydrolytic profile of CB-NTXOL-BUPOH, and thus helped in corroborating the hydrolysis model with the hydrolysis data. Estimation of the hydrolytic rate constants based on the hydrolysis model revealed the values of $k_1$, and $k_2$ as 0.0240±0.0007 hr$^{-1}$ and 0.0139±0.0006 hr$^{-1}$, respectively.

Figure 11:
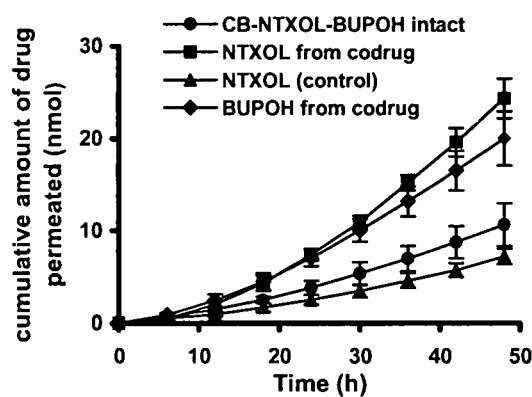
FIG. 11. is a representative permeation profile from saturated solutions of the carbonate codrug and 6-β-naltrexol (control) through human skin in vitro at 32° C. Data is represented as mean±SD (n=4 for CB-NTXOL-BUPOH treatment and n=3 for 6-β-naltrexol treatment).
Figure 12:
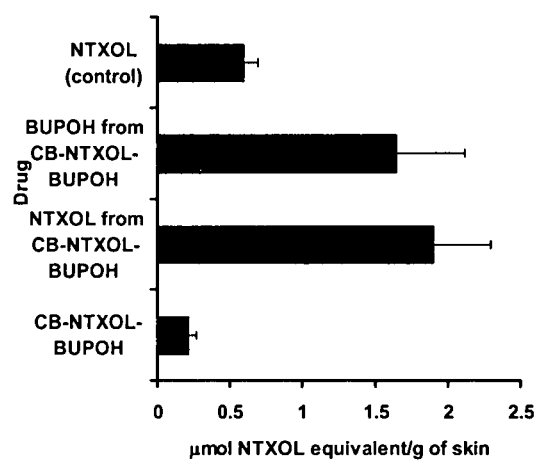
FIG. 12. shows the drug concentration of the carbonate codrug and parent drugs in the skin after a 48 h diffusion study following application of drugs as saturated solutions in light mineral oil. Data is represented as mean±SD.

The carbonate codrug was hydrolyzed on passing through human skin in vitro and appeared as a combination of intact codrug and the parent drugs, 6-β-naltrexol and hydroxybupropion, in the receiver compartment. The carbonate codrug was tested on skin from three different human donors, using four diffusion cells each. Because human skin exhibits wide inter-subject permeation variability, 6-β-naltrexol was used as a control on each human skin sample. A representative permeation profile is shown in FIG. 11. When cumulative 6-β-naltrexol equivalents permeated were compared after treatment with CB-NTXOL-BUPOH, approximately 35% of the 6-β-naltrexol flux was from intact CB-NTXOL-BUPOH and 65% was 6-β-naltrexol originating from the skin hydrolysis of CB-NTXOL-BUPOH. The cumulative amounts and flux values of regenerated 6-β-naltrexol were similar (p>0.05) to the values of hydroxybupropion, which further corroborates that these values were solely derived from transport and metabolism of CB-NTXOL-BUPOH. The maximum steady-state flux from the carbonate codrug in 6-β-naltrexol equivalents was four times higher than that from 6-β-naltrexol base alone as shown in Table 3. This represents a four-fold enhancement in the delivery of 6-β-naltrexol across skin after application of the carbonate codrug. A paired Student's t-test showed a significant difference between these means (p<0.05). Assuming that the minimum therapeutic dose of 6-β-naltrexol closely matches that of NTX and considering a 50-100 mg/day dose of NTX with an oral bioavailability range 5-40%, the daily dose range is 7-118 μmol. Therefore a therapeutic delivery rate of 6-β-naltrexol is in the range of 11-197 nmol·cm$^{-2}$·$^{-1}$. Although we were not able to deliver enough 6-β-naltrexol for therapeutic efficacy, this study provides some clear insight into what is needed to increase the delivery rates in future optimization studies. Transepidermal water loss (TEWL) measurements taken before and after the completion of the 48-hr diffusion study did not show any significant differences, indicating that no damage to the stratum corneum lipids or protein had occurred as a result of the drug or vehicle treatments.

Another explanation for the increased flux after topical application of CB-NTXOL-BUPOH is the added rapid bioconversion, which causes a difference in the concentration gradient profile for CB-NTXOL-BUPOH. It is well known that bioconversion rates of prodrugs can influence the flux of drugs (Yu et al., J. Pharm. Sci. 68 (1979) 1341-1357). Generally, prodrugs or mutual prodrugs are more lipophilic than the parent drugs and are therefore expected to partition very well into the lipid medium of the stratum corneum. Upon traversing the stratum corneum to the viable epidermis, they are bioconverted, predominantly in the viable tissue, into the relatively more hydrophilic parent drugs. The enzyme-rich viable epidermis provides a more aqueous environment to drug transport than the stratum corneum, so the parent drugs

TABLE 3

Properties of 6-β-naltrexol, hydroxybupropion, and the carbonate codrug, CB-NTXOL-BUPOH.

| Drug | Light mineral oil solubility (mM) | Hanks' buffer solubility (mM) | clogP† | SC/Vehicle partition coefficient, PC$^b$ | Flux from mineral oil (nmol cm$^{-2}$ h$^{-1}$) | Mean permeability coefficient ($K_P \times 10^3$), cm/h |
|---|---|---|---|---|---|---|
| CB-NTXOL-BUPOH | 2.88 ± 0.09 | 0.53 ± 0.01 | 3.71 | 200.61 ± 34.42 | 1.34 ± 0.35 | 0.47 |
| 6-β-naltrexol | 0.03 ± 0.01 | 0.30 ± 0.01 | 1.39 | 73.91 ± 22.10 | 0.36 ± 0.15 | 12.00 |
| Hydroxybupropion | 4.04 ± 0.04 | 3.85 ± 0.05 | 2.87 | ND$^a$ | 25.89 ± 6.01 | 6.41 |

$^a$Not determined
$^b$PC - SC/Vehicle partition coefficient has no units
SC—Stratum corneum
†Determined from Daylight ® 4.51 software Drug disposition data from the human skin samples used in the diffusion studies are summarized in FIG. 10. Significant levels of parent drugs regenerated from the carbonate codrug were detected in all of the donor skin samples used in this experiment. The mean molar percentage of regenerated 6-β-naltrexol to total drug extracted from the skin ranged from 56 to 86%. No significant difference in the concentrations of the regenerated parent forms, 6-β-naltrexol and hydroxybupropion, was found in the skin after application of the carbonate codrug. Human skin has substantial esterase activity, and the enzymes involved have been reported to be resistant to the stresses of freezing and storage (Collier et al., Toxicol. Appl. Pharmacol. 99 (1989) 522-533), which is why we see extensive bioconversion in the previously frozen skin experiments. Higher concentrations of CB-NTXOL-BUPOH in the skin either as intact form of the codrug or as parent drugs revealed that CB-NTXOL-BUPOH partitions into the skin better than 6-β-naltrexol (control), and these results were consistent with stratum corneum/vehicle partition coefficient studies.

To gain further insight into the mechanism of improved transport across skin, solubilities of the drugs in the donor compartment solution were determined. The mineral oil solubilities of 6-β-naltrexol, hydroxybupropion, and CB-NTXOL-BUPOH are shown in Table 3. CB-NTXOL-BUPOH had higher solubilities in both oil and aqueous media, as compared to 6-β-naltrexol. Based on the solvatochromic parameters of solubility, the increase in solubility of the carbonate codrug could largely be attributed to a lower melting point and a smaller heat of fusion than 6-β-naltrexol. The increased codrug solubility could have contributed to the increased skin diffusion flux rates ($J_{max}$) in vitro, although there is no direct relationship between the oil solubilities and flux values.

are able to traverse the viable epidermis at a faster rate than the more lipophilic codrug. As the parent drugs diffuse across the viable epidermis, they are swept away by the receiver solution as they would be by the microcirculation in vivo, thus maintaining standard sink conditions. The flux of the prodrug depends on the stratum corneum resistance and the viable tissue resistance, however, the chemical reaction term couched as the metabolic rate constant for bioconversion becomes rate determining as the viable tissue becomes the codrug sink. Therefore, codrugs that undergo fast bioconversion are not rate-limited by their transport through the viable tissue of the skin because they have primarily bioconverted to the more hydrophilic parent forms. Whereas lipophilic codrugs that undergo slower bioconversion to the parent compounds will have difficulty permeating the viable tissue due to their lower water solubility. Simultaneous transport and metabolism in the skin are relatable through a diffusion-bioconversion constant expressed as $$\sqrt{\frac{k}{D}},$$

where k is the metabolic rate constant for the codrug bioconversion, and D is the diffusivity of the drug in the viable tissue (Yu et al., J. Pharm. Sci. 68 (1979) 1341-1357). Highly lipophilic codrugs make the drugs more readily available in the skin via higher partitioning, as compared to the more hydrophilic parent drugs. In addition, making the hydrophobic codrug more labile to hydrolytic cleavage would decrease diffusional resistance across the viable tissue. Therefore, increasing the codrug diffusion-bioconversion rate constant expressed above would increase the flux of parent drugs in the same proportion.

2.5. Conclusion

A four-fold enhancement in the transdermal delivery of 6-β-naltrexol after carbonate codrug, CB-NTXOL-BUPOH, application was largely attributed to improvement in the physicochemical properties, including increased solubilities in both oil and aqueous media, higher drug partitioning into the skin, and rapid bioconversion. Although the flux of 6-β-naltrexol via codrug application did not meet the minimum necessary therapeutic delivery rate of about 11 nmol cm$^{-2}$ h$^{-1}$, the results are still promising because these flux values could be substantially increased in vivo where enzymatic conversion rates may be even higher than rates under in vitro conditions. Increased bioconversion rates in vivo would cause a steeper concentration gradient in the skin, and likely an increased flux of 6-β-naltrexol. Results from these studies provided valuable information for optimization of the codrug design and synthesis in order to achieve higher flux rates for therapeutic treatment.

Skin tissue was supplied by the National Cancer Institute Cooperative Human Tissue Network (CHTN).

Example 3

In Vivo Evaluation of a Transdermal Codrug of 6-β-naltrexol Linked to Hydroxybupropion in Hairless Guinea Pigs

3.1 Introduction

In this example, in vivo studies were carried out in a hairless guinea pig model to determine the percutaneous absorption of a transdermal codrug of 6-β-naltrexol.

3.2 Experimental

Materials

Hanks' balanced salts modified powder, sodium bicarbonate, and the internal standard, naloxone, were purchased from Sigma (St. Louis, Mo.). p-Phenylenediamine, ammonium acetate, ethyl acetate, trifluoroacetic acid (TFA), triethylamine (TEA), 4-(2-Hydroxyethyl)-1-piperazineethanesulfonic acid (HEPES), propylene glycol (PG), and acetonitrile (ACN) were obtained from Fisher Scientific (Fairlawn, N.J., USA). Ammonium citrate was obtained from Alfa Aesar (Ward Hill, Mass., USA). ARCARE® 7396 (pressure-sensitive tape with MA-38 medical grade acrylic adhesive and 60# Kraft release paper) was a gift from Adhesive Research, Inc. (Glen Rock, Pa.). MEDIFLEX® 1502 (backing membrane; pigmented metalized polyester) was a gift from Mylan Technologies Inc. (St. Albans, Vt.). SCOTCHPAK™ 9742, a fluoropolymer release liner and CoTran™ 9715, a 3 mil ethylene vinyl acetate (EVA) copolymer with 19% vinyl acetate were gifts from 3M™ Drug Delivery Systems (St. Paul, Minn.). Hill Top Chambers® were obtained from Hill Top Research, Inc. (Cincinnati, Ohio). Water was purified using a Barnstead nanopure Diamond Ultrapure water system (Barnstead International, Dubuque, Iowa, USA)

Synthetic Procedures

The detailed synthetic procedures for the preparation of 6-β-naltrexol, hydroxybupropion, and the carbonate codrug, CB-NTXOL-BUPOH, have been reported elsewhere (see Kiptoo et al., *J Control Release* 113 (2006) 137-45; Hamad et al., *Bioorg Med Chem* (2006); see also Example 1 herein). Synthesis of a transient intermediate, observed during chemical or enzymatic hydrolysis of the codrug to hydroxybupropion, has also been reported previously (Id.).

Plasma Hydrolysis of the Carbonate Codrug

Guinea pig plasma, which was stored at −20° C., was thawed to room temperature. Known and sub-saturated amounts of the codrug (50 nmol) were added to approximately 2.0 ml of the guinea pig plasma and vortexed. Two-hundred μl aliquots of the spiked plasma were distributed into sealed vials, and incubated at 37° C. Samples were withdrawn at predetermined time intervals; 0, 0.5, 1, 2, 4, 6, 9, 24, 30, and 48 h. 500 μl of ACN was added to each sample to precipitate plasma protein. Each sample was vortexed and centrifuged at 10,000×g for 15 min. The supernatant was separated and evaporated under nitrogen at room temperature, and the residue was reconstituted with ACN for high-pressure liquid chromatography (HPLC) analysis. A standard curve was prepared from drug-spiked plasma samples processed by the same method. The amounts of the codrug remaining or parent drugs released were plotted against time. These hydrolytic profiles were fit to previously developed mathematical models using nonlinear least-squares regression analysis (SCIENTIST®, Micromath Inc., Salt Lake City, Utah) as described by the equations below:

$$C_A = C_A^0 e^{-k_1 t} \qquad \text{Eq. (1)}$$

$$C_B = \frac{C_A^0 k_1}{k_2 - k_1} [e^{-k_1 t} - e^{-k_2 t}] \qquad \text{Eq. (2)}$$

$$C_C = C_A^0 + \frac{C_A^0}{k_1 - k_2} [k_2 e^{-k_1 t} - k_1 e^{-k_2 t}] \qquad \text{Eq. (3)}$$

$$C_D = C_A^0 (1 - e^{-k_1 t}) \qquad \text{Eq. (4)}$$

Where $k_1$ and $k_2$ are rate constants, $C_A^0$ is the initial concentration of the codrug, and $C_A$, $C_B$, $C_C$, and $C_D$ are the concentrations of the codrug, intermediate, hydroxybupropion, and 6-β-naltrexol at any time t, respectively.

Preparation of the Gel Formulation

A hydroxyethyl cellulose-based gel was prepared for topical application. First, either CB-NTXOL-BUPOH or 6-β-naltrexol (~25 mg each) was dissolved in 1 ml of PG:buffer, pH 7.4 (2:3, v/v) solution using a magnetic stirrer. Hydroxyethyl cellulose (2%, w/w) was dispersed into these mixtures, sonicated, vortexed, and allowed to form a gel at room temperature. The drug in each formulation was saturated, forming a suspension.

Permeation Studies in Guinea Pigs In Vivo

Male and female Hairless IAF and Hartley guinea pigs (Charles River) weighing 345-482 g were used for topical studies (n=5 to 6 per treatment group). Prior to surgery, the animals were treated with glycopyrrolate and buprenorphine (to induce analgesia), and then ketamine (100 mg/kg, i.p.) and xylazine (8 mg/kg, i.m.) were used for anesthetic purposes. Catheters were surgically implanted into the jugular vein. A "blank" baseline plasma sample was drawn from each animal immediately before drug treatment. 500 μL of the gel containing the drug was applied onto the dorsal region of the guinea pig with a syringe and subsequently spread to cover an area of 7.25 cm$^2$. A rubber ring fitted with a drug-impermeable backing laminate (MEDIFLEX® 1502) was used to enclose the area of gel application. ARcare® acrylic adhesive was used to ensure that the ring maintained contact with the skin. Additionally, a bio-occlusive tape was placed over the patches to further secure the formulation on the guinea pigs. Drug formulations were applied on both sides of each guinea pig to give a total application area of 14.5 cm$^2$. Plasma samples were obtained at predetermined time intervals, which included 48 h while the formulations were on the animal, and for another 48 h after patches and formulations were removed. Blood samples were immediately centrifuged at 10,000×g for 3 min, and the plasma was separated. Plasma samples were stored at −70° C. until analysis by liquid chromatographic mass spectrometry, LC-MS.

Plasma Sample Extraction Procedure

Exactly 500 μl of acetonitrile:ethyl acetate (1:1, v/v) was added to 100 μl of plasma sample in a 1.5 ml microcentrifuge tube, and the mixture was vortexed for 30 s and then centrifuged at 10,000×g for 20 min. The supernatant was decanted into a clean test tube and evaporated under nitrogen at 30° C. The residue was reconstituted with 100 μl of acetonitrile, vortexed, and sonicated for 5 min. The clear solution was placed into an HPLC vial containing low volume inserts, and 20 μl of the sample was injected onto the LC-MS column. The extraction efficiencies were 78.5±2.1%, 87.0±3.5%, and 81.6±2.2% for CB-NTXOL-BUPOH, hydroxybupropion, and 6-β-naltrexol, respectively. Data were corrected for the respective extraction efficiencies.

Quantitative Analysis

HPLC Conditions

A modified HPLC assay from Hussain et al. (Hussain et al., *Pharm Res* 5 (1988) 615-8) was used for the determination of the hydrolytic profile of CB-NTXOL-BUPOH. The HPLC system consisted of a Waters (Milford, Mass., USA) 717 Plus Autosampler, 1525 Binary Pumps, and a 2487 dual wavelength UV absorbance detector with Breeze software. A Brownlee Valueline $C_{18}$ reversed-phase Spheri5 column (220×4.6 mm, 5 μm) with a $C_{18}$ reversed-phase guard column (15×3.2 mm, 7 μm) was used with the UV/VIS detector set at a wavelength of 215 nm. The mobile phase consisted of acetonitrile (ACN): 0.1% TFA buffer adjusted with TEA to pH 3.0 (55:45). The flow rate of the mobile phase was 1.5 ml/min with 100 μl sample injections. Retention times on the column were found to be 2.3, 4.6, 5.2, and 10.5 min for 6-β-naltrexol, hydroxybupropion, intermediate, and CB-NTXOL-BUPOH, respectively. Standards were analyzed with each set of hydrolysis samples and linear regression of standard curves exhibited excellent linearity over the entire concentration range (50-1000 ng/mL) employed in the assays. The assay sensitivity was at least 20 ng/mL or better for all the drugs. Both intra-day and inter-day assays had small coefficients of variation (<10% CV) indicating that the method was reproducible, accurate, and precise.

LC-MS Conditions

LC-MS was employed in the analysis of guinea pig plasma samples to determine percutaneous absorption in hairless guinea pigs in vivo. Chromatography was performed on a Waters Symmetry $C_{18}$ (2.1×150 mm, 5 μm) column at 35° C. with a mobile phase consisting of ammonium acetate (2 mM) containing 0.01 mM ammonium citrate:acetonitrile (35:65 v/v) at a flow rate of 0.25 mL/min. A Waters Symmetry $C_{18}$ (2.1×10 mm, 3.5 μm) guard column was used. The volume of injection was 20 μL. The MS detection was performed using electrospray ionization (ESI) for ion production. Selected ion monitoring (SIM) was performed in the positive mode for CB-NTXOL-BUPOH, m/z 650 (dwell time, 0.30 s), 6-β-naltrexol, m/z 344, and BUPOH, m/z 238. Naloxone (m/z 324) was used as the internal standard. The capillary voltage was 4.5 kV and the cone voltage was 30 V. The source block and desolvation temperatures were 120° C. and 250° C., respectively. Nitrogen was used as a nebulization and drying gas at flow rates of 50 and 450 L/h, respectively. The retention times for 6-α-naltrexol, hydroxybupropion, naloxone (internal standard), and CB-NTXOL-BUPOH were 3.27±0.11, 4.32±0.20, 6.26±0.23, and 16.60±0.28 min, respectively.

Pharmacokinetic Analysis

Topical administration data were analyzed by non-compartmental analysis to determine mean steady-state plasma concentration ($C_{SS}$), lag time to steady-state ($t_{lag}$), and area under the curve from 0 to 48 h, $AUC_{0-48}$. The steady-state plasma concentration of the drug after application of the gel formulation containing either the codrug or 6-β-naltrexol was calculated by using the following equation:

$$C_{SS} = \frac{AUC_{0-t}}{time} \quad (5)$$

Fabrication of Transdermal Systems of 6-β-naltrexol and p-phenylenediamine

The transdermal patches of 6-β-naltrexol base (7.25 cm²) were fabricated by sandwiching a drug reservoir between a drug-impermeable backing laminate (MEDIFLEX®1502) and a rate-controlling EVA membrane (CoTran™ 9715) with ARcare®7396 adhesive. A release slip composed of SCOTCHPAK™ 9742 was used to leave a small opening into the reservoir of the empty device. The membrane/adhesive laminate was then heat sealed to the metallized polyester backing membrane. The slip was removed to form a small port, and 500 μL of the saturated drug solution (24 mg/mL) of 6-β-naltrexol in 3:1 (v/v) of propylene glycol:buffer pH 7.4 was injected into the reservoir. After injecting the drug solution into the reservoir, the port was heat sealed. Molded plastic Hill Top Chambers® (25 mm diameter) were used for β-phenylenediamine studies. A non-woven cotton Webril® pad was placed in each chamber to hold the test material. Hill Top Chambers® were then inserted into the patch by cutting a hole in the rate-controlling membrane so that the Webril® pad would be in direct contact with the skin. The patches were made with the same materials as described for 6-β-naltrexol. Five-hundred μL of the drug solution was added to the Webril® pad just before patch application on the guinea pig.

Animal Studies

Statistical Analysis

Statistical analysis of the pharmacokinetic parameters obtained after the topical application studies were computed with a one-way ANOVA followed by Tukey's post hoc analysis using SIGMA-STAT (SPSS, Chicago, Ill.). Data were reported as mean±S.D and were considered to be significant at p<0.05.

3.3 Results and Discussion

Figure 13:
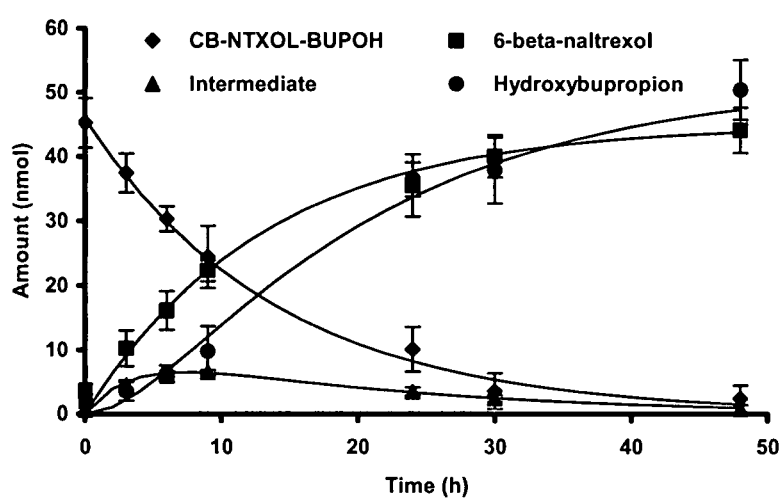
FIG. 13. is a hydrolysis profile of the carbonate codrug, CB-NTXOL-BUPOH, in guinea pig plasma at 37° C.

Esterases, which are ubiquitously found in most tissues and plasma have been reported to be resistant to the stresses of freezing and storage (Ascher, et al., *Journal of Clinical Psychiatry* 1995, 56 (9), 395-401). It is expected that this codrug should be converted back to the parent drugs by chemical and enzymatic hydrolysis. FIG. 13 shows the hydrolytic profile of the carbonate codrug, forming the two active parent drugs, hydroxybupropion and 6-β-naltrexol, in guinea pig plasma. The degradation half-life of the codrug in guinea pig plasma was approximately 8.7 hrs. We expected the regeneration of 6-β-naltrexol from the codrug to involve a one-step reaction, and this was also confirmed by the appearance of 6-β-naltrexol with a similar half-life to that of the disappearance of the codrug. Compared to the previously reported codrug half-life of 29 hrs in isotonic pH 7.4 phosphate buffer (Kiptoo et al., *J Control Release* 113 (2006) 137-45) as shown in Table 4, the codrug undergoes an almost three-fold faster hydrolysis in guinea pig plasma in vitro, largely attributed to the added catalysis by the esterase enzymes. However, the release of hydroxybupropion proceeded through a two-step process and therefore had a longer half-life compared to 6-β-naltrexol. Although the regeneration of the two parent drugs, 6-β-naltrexol and hydroxybupropion, occurred through different pathways, molar concentrations of hydroxybupropion either completely or partly regenerated (the intermediate) were stoichiometrically equivalent to that of 6-β-naltrexol. This clearly indicated that regeneration of the parent drugs was solely derived from the codrug with no other non-transient intermediates. In vitro enzymatic hydrolysis not only confirms that hydrolysis of the codrug would release the two active parent drugs in the skin and/or in the body, but also helps in the evaluation of the impact of these rates of bioconversion on the transport of drugs across the skin.

Figure 14:
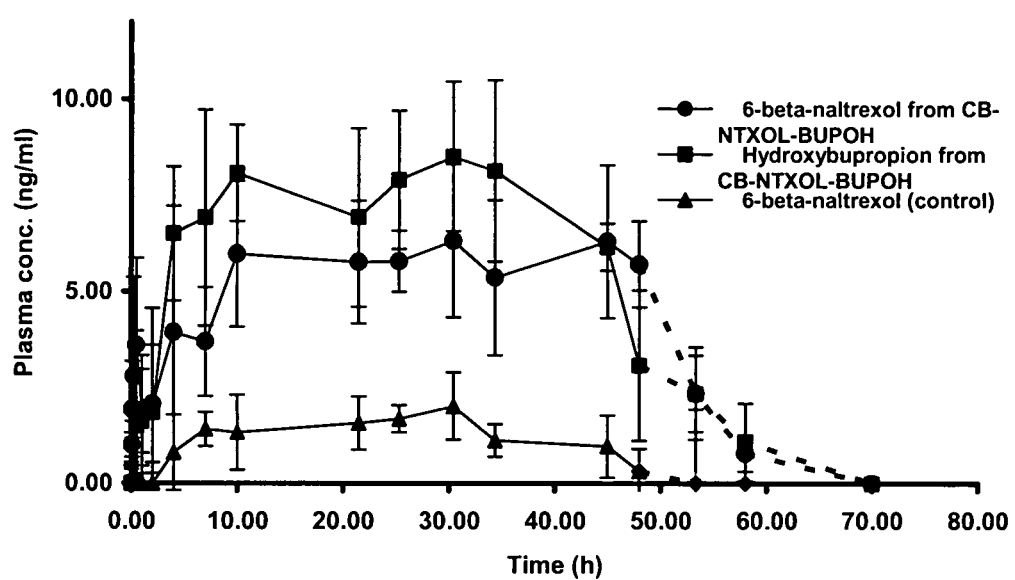
FIG. 14. shows mean (±S.D.) plasma concentration profiles in guinea pigs after topical application of a gel formulation containing either CB-NTXOL-BUPOH (n=6) or 6-β-naltrexol (control, n=5). The dotted line (----) indicates the plasma concentration after the removal of the formulation.

As shown in Table 4, the experimental half-lives for the regeneration of the two active parent drugs, hydroxybupropion and 6-β-naltrexol, in guinea pig plasma in vitro were longer than optimally desired for rapid biotransformation immediately post absorption. However, in vivo guinea pig plasma samples post-CB-NTXOL-BUPOH topical application contained only trace amounts of intact codrug. In vitro human skin diffusion studies showed significant amounts of CB-NTXOL-BUPOH diffusing through the skin intact, therefore, it appears logical that the codrug biotransforms rapidly in the guinea pig in a tissue other than the plasma. Other prodrugs containing highly and moderately branched groups have also been shown to exhibit longer plasma half-lives as a result of steric hindrance in the vicinity of the carbonyl linkage, and therefore decreased hydrolysis rates occur (Carvalho et al., *Bioorg Med Chem* 8 (2000) 1719-25; Safadi et al., *Pharm Res* 10 (1993) 1350-5; Vaddi et al., *Pharm Res* 22 (2005) 758-65). Additionally, the short carbonyl chain introduces some rigidity thus making the linkage less accessible.

are shown in FIG. 14. The pharmacokinetic parameters, including $C_{max}$, $T_{max}$, $C_{SS}$, $AUC_{0-48}$, and $T_{lag}$ are given in Table 5.

TABLE 5

Pharmacokinetic parameters of 6-β-naltrexol after application of a gel formulation containing either CB-NTXOL-BUPOH or 6-β-naltrexol base (control). Data is represented as mean (±S.D.)

| Parameter | NTXOL | NTXOL from CB-NTXOL-BUPOH |
|---|---|---|
| $AUC_{0-48}$(ng/ml*h) | 66.4 ± 7.9 | 282.0 ± 14.5 |
| $C_{max}$(ng/ml) | 1.5 ± 0.2 | 6.6 ± 0.4 |
| $T_{max}$(h) | 28.1 ± 1.5 | 10.1 ± 0.9 |
| $T_{lag}$(h) | 5.1 ± 0.7 | 5.0 ± 1.1 |
| Observed $C_{SS}$(ng/ml) | 1.2 ± 0.5 | 6.4 ± 0.9 |
| Predicted $C_{SS}$(ng/ml)* | 0.2 ± 0.1 | 0.7 ± 0.3 |
| Enhancement factor | 1 | 5.3 |

*Predicted from in vitro human skin diffusion data

6-β-naltrexol equivalent steady state plasma concentrations of 6.40±0.93 ng/ml after application of the codrug were maintained for 48 h, as compared to 1.25±0.51 ng/ml observed for the control animals. Increased percutaneous absorption of 6-β-naltrexol after application of the codrug is further demonstrated by the significantly higher AUC value (p<0.05). Only trace amounts of the codrug and the intermediate (m/z 282), that follows from hydrolysis of the codrug into hydroxybupropion, were observed in some of the plasma samples, but no further effort was made towards quantifica-

TABLE 4

Permeation properties of 6-β-naltrexol, hydroxybupropion, and the codrug, CB-NTXOL-BUPOH
Data is represented as mean (±S.D)

| Drug | Light mineral oil solubility (mM)[‡] | Half-life in buffer, pH 7.4 (h)[‡] | Guinea pig plasma half-life (h) | In vitro flux (nmol cm$^{-2}$ h$^{-1}$)[‡] | In vitro lag time (h)[‡] |
|---|---|---|---|---|---|
| 6-β-naltrexol | 0.03 ± 0.01 | stable | stable | 0.36 ± 0.15 | 15.72 ± 1.76 |
| CB-NTXOL-BUPOH | 2.88 ± 0.09 | 28.9 | 8.7 | 1.34 ± 0.35[‡‡] | 12.10 ± 0.77[‡‡] |
| Hydroxybupropion | 4.04 ± 0.04 | stable | stable | 25.89 ± 6.01 | 7.83 ± 1.73 |

[‡]Values obtained from Kiptoo et al. [2].
[‡‡]NTXOL equivalent flux in human skin A slightly modified LC-MS assay from Valiveti et al (Valiveti et al., *J Chromatogr B Analyt Technol Biomed Life Sci* 810 (2004) 259-67) was used to quantify the amounts of CB-NTXOL-BUPOH, hydroxybupropion, and 6-β-naltrexol in guinea pig plasma following in vivo transdermal application of CB-NTXOL-BUPOH or 6-β-naltrexol (control). CB-NTXOL-BUPOH, hydroxybupropion, and 6-β-naltrexol peaks were well resolved and free of interference from endogenous compounds in the plasma. No significant matrix effect was observed for the analytes in the plasma samples. Results of the intra-day and inter-day validation assays indicated that the accuracy of the assay was >92% and the coefficient of variation did not exceed 10%. The lower limit of quantification (LLOQ) was 0.5 ng/ml for CB-NTXOL-BUPOH and hydroxybupropion, and 0.75 ng/ml for 6-β-naltrexol. The post-preparative stability studies indicated that the stabilities of CB-NTXOL-BUPOH, hydroxybupropion, and 6-β-naltrexol were greater than 94% for at least 48 h at 12° C., which corresponds with the autosampler temperature.

The plasma concentration profiles of the analytes following topical applications of gel formulations containing either CB-NTXOL-BUPOH or 6-β-naltrexol in hairless guinea pigs tion. Overall, this represented a significant five-fold (p<0.05) enhancement in the delivery of 6-β-naltrexol via the codrug strategy. As illustrated in FIG. 3, no significant skin reservoir effect was observed in guinea pigs, as plasma levels of each of the studied drugs declined after the removal of the gel formulation at rates similar to their systemic elimination rates. Also, observed in vivo lag times were significantly shorter than lag times observed in vitro. Often flow-through diffusion cells used for in vitro studies artificially add extra time to lag times seen in vivo. On the other hand, short in vivo lag times could be attributed to significant contributions from the shunt routes through the stratum corneum for the large codrug molecule, or to an increased in vivo bioconversion rate as compared to the in vitro rate of the carbonate linked codrug. Large and/or polar drugs can be carried through the stratum corneum via paths of least resistance provided by the shunt routes. These routes avoid the tortuous pathway of the stratum corneum phospholipid bilayers and thus have minimal lag times Scheuplein, *J Invest Dermatol* 48 (1967) 79-88; Wallace and Barnett, *J Pharmacokinet Biopharm* 6 (1978) 315-25). Additionally, reduced lag times could be due to increased bioconversion of the carbonate linked codrug. The more lipophilic codrug has increased partitioning into the stratum corneum (Kiptoo et al., *J Control Release* 113 (2006) 137-45) and once in the skin, it is reverted back chemically or enzymatically to the more hydrophilic parent drugs, hydroxybupropion and 6-β-naltrexol. These more hydrophilic parent drug forms should be able to traverse the viable epidermis faster than the large lipophilic codrug and potentially result in shorter lag times.

Predicting Plasma Concentrations from In Vitro Permeation Studies

To predict the plasma concentration of 6-β-naltrexol after application of the gel formulation containing either the codrug or the control formulation, the following equation was used:

$$C_{SS} = \frac{J_{SS}A}{Cl} \quad (4)$$

where $C_{SS}$ is the predicted steady state plasma concentration (ng/ml); $J_{SS}$ is the steady-state flux from in vitro permeation in Table 4 from previous studies; A is the area of the skin in contact with the formulation (14.5 cm$^2$); Cl is the total body clearance. Pharmacokinetic parameters such as total body clearance were previously investigated after intravenous administration of 6-β-naltrexol (50 mg/kg) in guinea pigs [25]. In the current study, the predicted steady state plasma concentrations of 6-β-naltrexol equivalents were 0.7±0.3 ng/ml and 0.2±0.1 ng/ml following topical application of CB-NTXOL-BUPOH and 6-β-naltrexol, respectively. Although the predicted steady-state plasma concentration of 6-β-naltrexol following topical application of CB-NTXOL-BUPOH and 6-β-naltrexol were significantly lower (p<0.05) than the observed values, the lower values can largely be attributed to the use of human skin to conduct in vitro studies. In previous experiments with 6-β-naltrexol, flux and other in vitro permeation parameters were found to be 5.6-fold greater in guinea pig skin than in human skin (Hussain et al., J. Pharm. Sci. 76 (1987) 356-358). Guinea pig skin is often more permeable than human skin, especially when the stratum corneum is the major rate-limiting step in the absorption process. The decreased guinea pig skin resistance, as compared to human skin, is likely due to the lack of a multi-layered (only a few layers in the guinea pig) stratum corneum structure. If the 5.6-fold factor is taken into account in the plasma level prediction equation, then the plasma levels from 6-β-naltrexol would be predicted at 1.1 ng/ml (quite close to the observed value of 1.2 ng/ml) and those of CB-NTXOL-BUPOH at 3.9 ng/ml (significantly different than the observed value of 6.4 ng/ml). The larger disagreement of the CB-NTXOL-BUPOH with the in vitro/in vivo correlation could be due to the added complications of potential inter-species differences in bioconversion rates that can influence the overall flux of 6-β-naltrexol from the codrug.

The increased flux of CB-NTXOL-BUPOH through guinea pig skin in vivo can be explained by the increased hydrophobicity and rapid bioconversion of the codrug as compared to the 6-β-naltrexol control treatment. As shown in Table 4, CB-NTXOL-BUPOH had a higher oil, solubility compared to 6-β-naltrexol (2.88±0.09 mM vs 0.03±0.01 mM). Hydrophobicity of a drug is well reflected in its relative ability to partition between oil and water. Since the lipophilicity of the lipid bilayer domain in the stratum corneum (SC) is much higher than that of water, a lipophilic compound would partition into the SC in preference to water (Scheuplein and Bronaugh, In: Goldsmith La. (ed) Biochemistry and physiology of the skin. *Oxford University Press, Oxford* vol 1 (1983) 1255-1294). A preferentially oil soluble drug should partition with ease into the SC, however may have difficulty leaving the stratum corneum and permeating through the viable tissue. As such, once CB-NTXOL-BUPOH becomes available in the skin following partitioning into the SC, it is rapidly converted into the more hydrophilic parent drugs, hydroxybupropion and 6-β-naltrexol. The more hydrophilic forms cross the viable epidermis and dermis meeting less resistance than the more lipophilic codrug. Simultaneous transport and metabolism in the skin are relatable through a diffusion-bioconversion constant expressed as $$\sqrt{\frac{k}{D}},$$

where k is the metabolic rate constant for the codrug bioconversion, and D is the diffusivity of the drug in the viable tissue [36]. It is possible that in vivo studies provide a higher level of enzymatic activity, potentially giving a higher diffusion-bioconversion constant which subsequently results in a higher flux.

3.4 Conclusion

The present investigation was an in vivo evaluation of a codrug of 6-β-naltrexol linked to hydroxybupropion, CB-NTXOL-BUPOH, for the eventual purpose of increasing the therapeutic efficacy of 6-β-naltrexol via a transdermal dosage form. The carbonate codrug was hydrolyzed on passing through skin and appeared in guinea pig plasma mainly as parent drugs, 6-β-naltrexol and hydroxybupropion. Only trace amounts of the codrug were detected in plasma. The codrug traversed the skin at a faster rate than 6-β-naltrexol. 6-β-naltrexol mean steady state plasma concentrations of 6.4 ng/ml were obtained after topical application of the codrug compared to 1.2 ng/ml from 6-β-naltrexol base, representing a five-fold enhancement in the transdermal delivery of 6-β-naltrexol. Overall, this study demonstrated that the codrug strategy could be used to enhance transdermal delivery of 6-β-naltrexol and thereby improve its therapeutic efficacy.

While the present invention has been described with reference to specific embodiments, this application is intended to cover those various changes and substitutions that may be made by those of ordinary skill in the art without departing from the spirit and scope of the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

All publications cited herein are hereby incorporated by reference in their entirety.

What is claimed is:

1. A codrug comprising:
   (a) hydroxybupropion; and
   (b) an opioid antagonist or an opioid agonist selected from the group consisting of Naltrexone, Buprenorphine, Butorphanol, Codeine, Dihydrocodeine, Dihydromorphine, Ethylmorphine, Hydromorphone, Levallorphan, Levorphanol, Nalbuphine, Nalmefene, Nalorphine, Naloxone, 6-β-Naltrexol, Phenazocine, Pholcodine, and 6-α-Naltrexol;
   wherein hydroxybupropion is linked via a carbonate linker to the opioid antagonist or opioid agonist to form a single chemical entity.

2. The codrug of claim 1, wherein said carbonate linker is cleavable.

3. The codrug of claim 2, wherein said carbonate linker is cleavable via hydrolysis and/or enzymatic digestion.

4. The codrug of claim 1, wherein said codrug comprises Naltrexone or 6-β-Naltrexol.

5. The codrug of claim 4, wherein said codrug comprises 6-β-Naltrexol.

6. The codrug of claim 4, wherein said codrug comprises Naltrexone.

7. A transdermal patch comprising a substrate and a layer of the codrug of claim 1.

8. A codrug having the following structure:

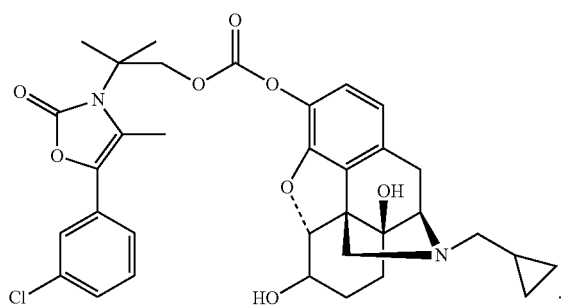

9. A codrug having the following structure:

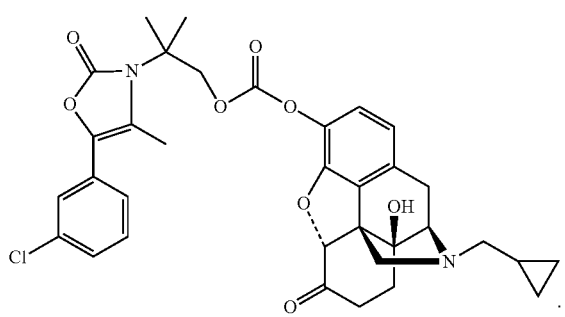

10. A codrug having the following structure:

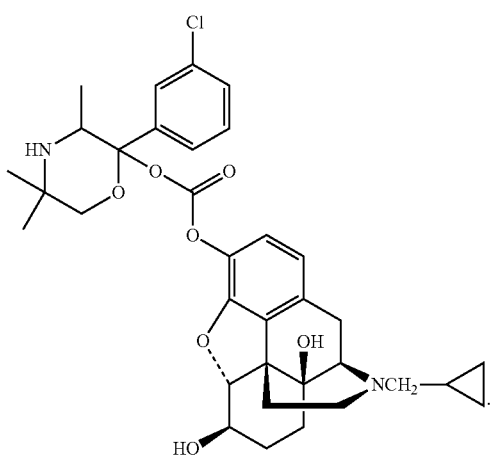

11. A codrug having the following structure:

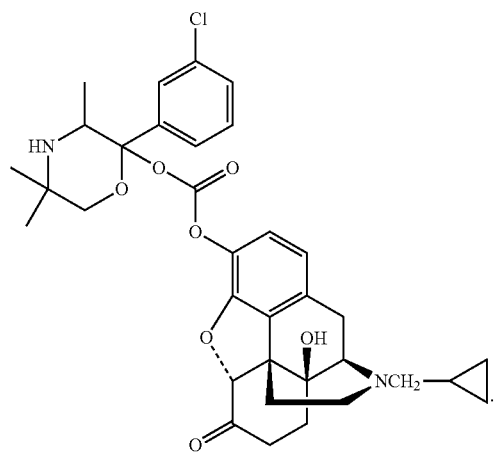

12. A codrug having the following structure:

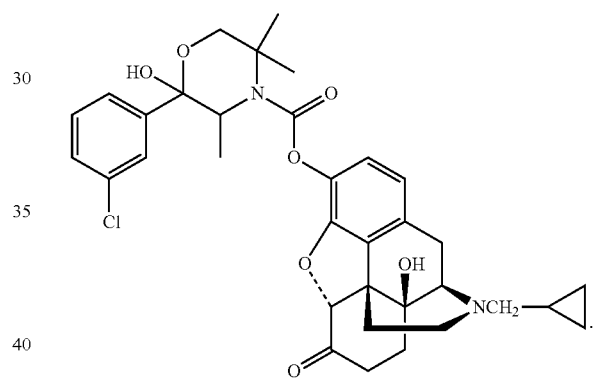

13. A codrug having the following structure:

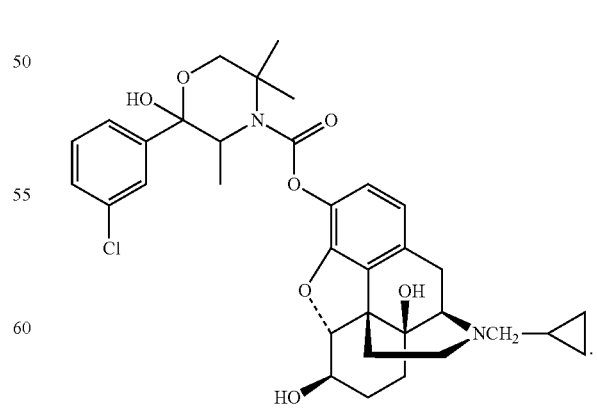

* * * * *